(12) United States Patent
Roberts et al.

(10) Patent No.: US 6,926,912 B1
(45) Date of Patent: Aug. 9, 2005

(54) METAL COMPOUNDS, MIXED OR SULPHATED, AS PHOSPHATE BINDERS

(75) Inventors: Norman B Roberts, Liverpool (GB); Maurice Webb, Chester (GB); Benjamin J Rankin, York (GB)

(73) Assignee: Ineos Silicas Limited, Warrington (GB)

( * ) Notice: Subject to any disclaimer, the term of this patent is extended or adjusted under 35 U.S.C. 154(b) by 0 days.

(21) Appl. No.: 09/508,923

(22) PCT Filed: Sep. 18, 1998

(86) PCT No.: PCT/GB98/02834

§ 371 (c)(1), (2), (4) Date: Jun. 19, 2000

(87) PCT Pub. No.: WO99/15189

PCT Pub. Date: Apr. 1, 1999

(30) Foreign Application Priority Data

Sep. 19, 1997 (GB) .............................................. 9720061

(51) Int. Cl.[7] ......................... A61K 33/26; C01B 31/24; C01G 49/02

(52) U.S. Cl. ..................... 424/647; 423/263; 423/420.2; 423/463; 423/518; 423/594.2

(58) Field of Search .............................. 423/263, 420.2, 423/463, 518, 594.2, 138, 157.4, 164, 165, 166, 430, 554, 555, 592, 593.1, 594.1, 544, 594, 157, 21.1, 140, 21.2, 230, 593, 633, 635, 636; 424/647, 600, 663, 682, 686, 688, 692, 693, 696, 697, 709, 715, 722; 23/304

(56) References Cited

U.S. PATENT DOCUMENTS

| | | | |
|---|---|---|---|
| 3,743,098 A | | 7/1973 | Martinez et al. |
| 4,786,510 A | * | 11/1988 | Nakel et al. ................... 426/74 |
| 4,970,079 A | * | 11/1990 | Hem et al. ................... 424/646 |
| 4,994,283 A | * | 2/1991 | Mehansho et al. ............ 426/74 |

(Continued)

FOREIGN PATENT DOCUMENTS

| | | | |
|---|---|---|---|
| DE | 3402878 A1 | * | 8/1985 |
| DE | 34 02 878 A | | 8/1985 |
| GB | 2 254 556 A | | 10/1992 |
| HU | 173556 | | 6/1979 |

(Continued)

OTHER PUBLICATIONS

Raki et al. "Preparation, Characterization, And Moss bauer Spectroscopy . . . " *Chem. Mater.*, vol. 7, pp. 221–224, 1995.*

Hansen et al. "Synthesis and characterization of pyroaurite" *Applied Clay Science* 10 (1995) pp. 5–19, no month.

Zhang et al. "Synthesis of Mg/Fe pyroaurite–like compounds and their anion exchange characteristics" *Inorganic Materials* 2:259 (1995) pp. 480–485, no month.

(Continued)

*Primary Examiner*—Wayne A. Langel
(74) *Attorney, Agent, or Firm*—Mayer Brown Rowe & Maw LLP

(57) ABSTRACT

A non-aluminum containing mixed metal compound for pharmaceutical use, which may, for example, be a mixed metal hydroxy carbonate containing magnesium and iron, and may have a hydrotalcite structure, preferably a non-aged hydrotalcite structure. Other metals, including, for example, calcium, lanthanum and cerium, may also be used. Metal sulphate compounds, especially calcium sulphate, lanthanum sulphate and/or cerium sulphate, compounds are also useful. The mixed metal compounds have a phosphate binding capacity of at least 30%, by weight, based on the test methods 1, 2 or 3, described in the specification, over a pH range from 3 to 7, such as from 2 to 8. The compound is especially useful in the treatment of hyperphosphataemia.

10 Claims, 10 Drawing Sheets

Effect of pH and ageing on percentage phosphate binding of mixed metal compounds

U.S. PATENT DOCUMENTS

| | | | | |
|---|---|---|---|---|
| 5,173,284 | A | * 12/1992 | Moisset et al. | 423/555 |
| 5,571,336 | A | 11/1996 | Wurzburger et al. | 134/2 |
| 5,654,011 | A | 8/1997 | Jackson et al. | 424/635 |
| 5,846,426 | A | * 12/1998 | Boos et al. | 20/645 |
| 5,968,976 | A | * 10/1999 | Murrer | 514/492 |
| 6,103,126 | A | * 8/2000 | Boos et al. | 210/645 |
| 6,174,442 | B1 | * 1/2001 | Geisser et al. | 210/645 |

FOREIGN PATENT DOCUMENTS

| | | |
|---|---|---|
| HU | 201880 | 1/1991 |
| JP | 5-155776 A * | 6/1993 |
| JP | 051155776 A | 6/1993 |
| WO | WO 92/01458 | 2/1992 |
| WO | WO 94/09798 | 10/1993 |
| WO | 96/30029 A | 10/1996 |
| WO | 97/22266 A | 6/1997 |

OTHER PUBLICATIONS

Reichle "Synthesis of anionic clay materials (mixed metal hydroxides, hydrotalcite)" *Solid State Ionics* 22 (1986) pp. 135–141, no month.

Zhang et al., "Phosphorous anion–exchange characteristics of a pyroaurite–like compound" *Inorganic Materials* 4 (1997) 132–138, no month.

Ulibarri et al. "Kinetics of the thermal dehydration of some layered hydroxycarbonates" *Themochimica Acta* 135 (1988) 231–236, no month.

Ookubo et al., "Hydrotalcites as Potential Adsorbents of Intestinal Phosphate" *Journal of Pharmaceutical Sciences* 81:11 (Nov. 1992) 1139–1140.

Spengler et al., "Cross–linked iron dextran is an efficient oral phosphate binder in the rat", *Nephrol. Dial. Transplant.* 11(1996) 808–812.

Patent Abstracts of Japan, vol. 017, No. 551 (C–1117) Oct. 5, 1993 for JP 05 155776 A (Otsuka Pharmaceut Factory Inc), Jun. 22, 1993 see.

Patent Abstracts of Japan, vol. 011, No. 371 (C–462), Dec. 3, 1987 for JP 62 145024 A (Asahi Chem Ind Co Ltd), Jun. 29, 1987 see abstract.

Database WPI, Week 7832 Derwent Publications Ltd., London, GB; An 78–58210A XP002091239 for SU 414 849 A (Khark House Build) Oct. 18, 1977 see abstract.

Patent Abstracts of Japan, vol. 010, No. 194 (C–358), Jul. 8, 1986 for JP 61 036222 A (Chugai Pharmaceut Co Ltd.), Feb. 20, 1986 see abstract.

Budavari et al, Eds.: "The Merck Index" Merck & Co Inc. XP002091238 see p. 917, left–hand column, line 1–6 see p. 331, right–hand column–p. 332, left–hand column, line 4–7 see p. 277, right–hand column.

* cited by examiner

Effect of pH and ageing on percentage phosphate binding of mixed metal compounds Effect of increasing weight of compound on percentage phosphate bound at pH3

Phosphate binding by the magnesium ferric iron and calcium magnesium ferric iron preparations over the pH range 3-8

Phosphate binding by aluminium hydroxide, magnesium hydroxide and calcium carbonate over the pH range 3-8

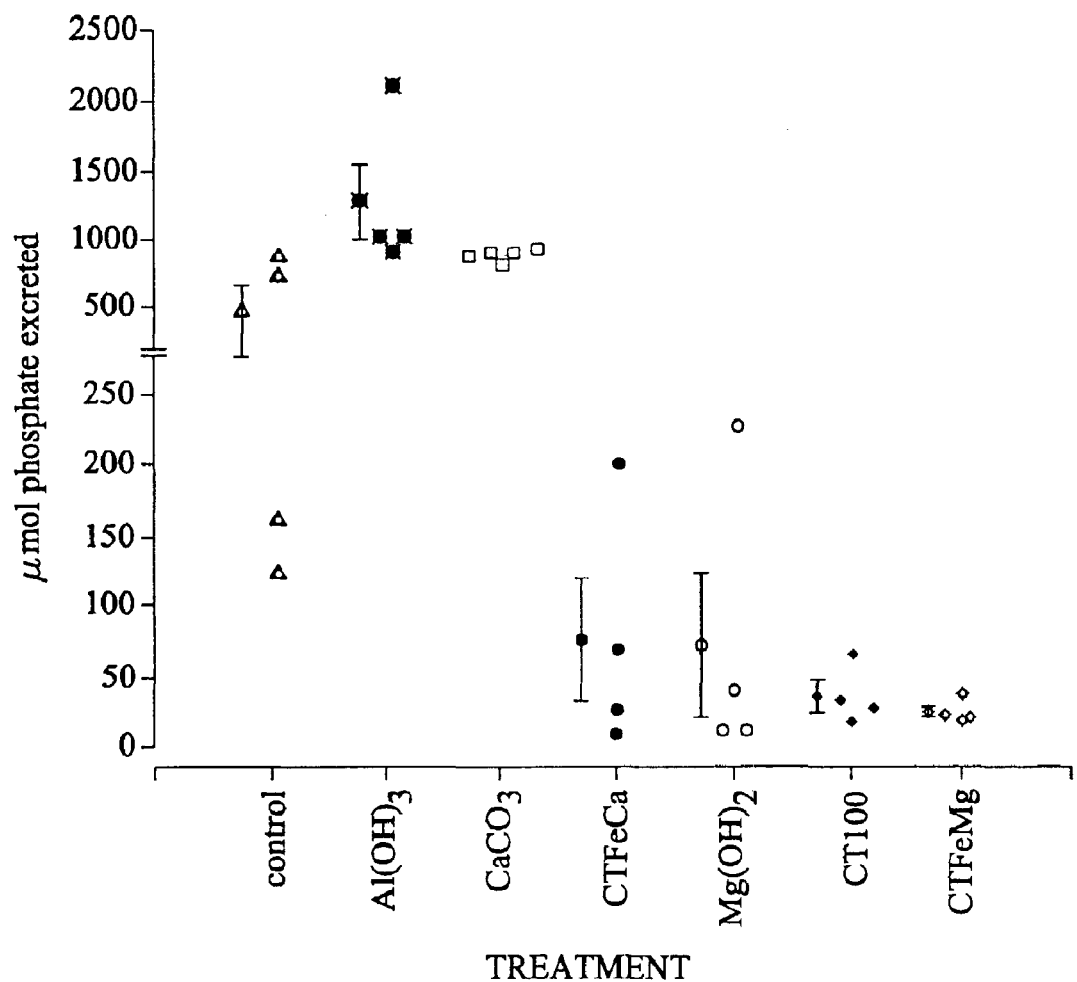

FIG. 9

Individual and mean (±1SEM) urinary phosphate excretion for control rats and those treated with phosphate binding compounds.
Individual values of urinary phosphate excretion (μmol/24 hours) were plotted for controls (△) and animals treated with Al(OH)$_3$(■), CaCO$_3$(□), CTFeCa(●), Mg(OH)$_2$(○), CT100 (♦) and CTFeMg (◇). Mean (±SEM) for each group are presented by points with error bars. *p<0.05 compared to Al(OH)$_3$ treated animal groups.

Mean (+1SEM) soluble faecal phosphate ($g^{-1}$ dry weight as a percentage of total soluble and unsoluble) faecal phosphate ($g^{-1}$ dry weight) for control rats and those treated with phosphate binding compounds.

* $p<0.05$ compared to control and $CaCO_3$ treated animals
△ $p<0.05$ compared to $CaCO_3$ treated animals

METAL COMPOUNDS, MIXED OR SULPHATED, AS PHOSPHATE BINDERS

This application is the national phase of international application PCT/GB98/02834 filed Sep. 18, 1998 which designated the U.S.

This invention relates to metal compounds, especially metal compounds free from aluminium, for pharmaceutical application, especially as phosphate binders.

WO-A-94/09798 discloses mixtures or complexes containing calcium and sulphate for use in a wide variety of pharmaceutical applications. The mixtures or complexes are inorganic compositions derivable from peat, in the form of aqueous solutions or synthetic syngenite ($CaSO_4.K_2SO_4.H_2O$) materials. There is no reference to their phosphate binding capacity.

In patients with kidney failure on haemodialysis (of whom there are 6,000,000 world wide), phosphate concentrations in the blood plasma can rise dramatically and such hyperphosphataemia can result in calcium phosphate deposition in soft tissue. Currently, the plasma phosphate levels are reduced by oral intake of inorganic and organic phosphate binders. The most common treatment in the UK is with aluminum hydroxide gel ("ALUDROX®" at 4 g/day) which forms an insoluble aluminum phosphate. However, this results in further toxic complications due to Al accumulation, eg reduction in heamoglobin production, impairment in natural repair and production of bone and possible impairment of neurological/cognitive function. Improvements in phosphate binding capacity as compared with aluminum hydroxide gel have been achieved with other aluminum compounds such as microcrystalline aluminum oxide hydroxide (boehmite) and certain hydrotalcites have been made; Ookubo et al, Journal Pharmaceutical Sciences (November 1992), 81(11), 1139–1140. However, such compounds still result in an intolerable amount of aluminum accumulation in renal failure patients. It is also known to use calcium compounds having pool solubility at pH 6–9, eg calcium carbonate, hydroxide, oxide and/or sulphate in a medicinal form resistant to gastric juices. However, it is known that, for example, with calcium carbonate, a large dosage is required because of its relatively low in vivo capacity for phosphate removal, such large dosages also being difficult to administer. This can cause fewer complications associated with high calcium intake. It has also been proposed (WO-A-92/01458) to control serum phosphate levels in patients suffering from or predisposed to hyperphosphataemia by contacting ingested phosphate with an oxy-iron compound selected from ferric oxides, oxy-hydroxides and hydroxides. Similarly, Spengler et al, Nephrol. Dial. Transplant. (996), 11, 808–812, suggests treatment of hyperphosphataemia with a complex of iron (III) oxide-hydroxide modified dextran. However, in the tests conducted, extremely high dosage amounts to animals were given. Moreover, many inorganic preparations are efficient phosphate binders only over a limited pH range, especially an acid pH range of about 3–5. Such current phosphate binders effective at pH3 would not necessarily bind as effectively at higher pH, eg $\geq 7$, which obtain in the lower tract, eg duodenum and below, and where at least some of the binding of phosphate may take place. Moreover, paticularly alkaline binders could buffer the stomach pH up to a high level at which they would not have a phosphate binding capacity.

Thus, there is an urgent and widespread need for a phosphate binder which does not release aluminium into the blood stream, which does not provide long term side effects, which can be administered in relatively low dosages and which is effective over a wide pH range of from say 2–8.

We have found surprisingly that certain mixed metal compounds, which are free from aluminium, may bind at least 30% by weight of the total weight of phosphate present over a pH range of from 2–8.

Thus, according to a first aspect, the invention provides a mixed metal compound for pharmaceutical use which is free from aluminium and which has a phosphate binding capacity of at least 30%, by weight of the total weight of phosphate present, over a pH range of from 2–8.

According to a second aspect, the invention provides the use, in the preparation of a medicament for treating hyperphosphataemia, of a mixed metal compound free from aluminium and having a phosphate binding capacity of at least 30%, by weight of the total weight of phosphate present, over a pH range of from 2–8.

Such mixed metal compounds may contain iron (III) and at least one of magnesium, calcium, lanthanum and cerium.

Preferably the mixed metal compounds contain at least one of hydroxyl and carbonate anions and optionally additionally, at least one of sulphate, chloride and oxide.

It is believed that preferred mixed metal hydroxy carbonates containing each of magnesium and iron are of a hydrotalcite structure. For such mixed metal compounds, it is generally preferable to use unaged hydrotalcites, which have not been subjected to a drying operation.

However, it is even more preferable to use mixed calcium/ferric mixed metal compound which seem to be equally effective whether unaged or not.

Even more preferably, the ratio of $Ca^{2+}:Fe^{3+}$ is at least 2:1, still more preferably at least 3:1.

An alternative preferred compound contains $Ca^{2+}$, $Mg^{2+}$ and $Fe^{3+}$, more preferably in a ratio of 3:3:2.

Further investigation of calcium rich compounds led us to find that although anhydrous calcium sulphate as such is a poor phosphate binder, after treatment of calcium sulphate, for example, anhydrous calcium sulphate, with an alkaline material, it became an extremely effective phosphate binder. This result is particularly surprising.

We predict also that each of lanthanum and cerium sulphate will behave similarly.

Thus, according to another aspect, the invention provides metal sulphate material for pharmaceutical use, which metal sulphate material is selected from at least one of calcium, lanthanum and cerium sulphate compounds treated with an alkali solution, preferably an aqueous solution of an alkaline hydroxide, more preferably sodium hydroxide, which said material comprises a solid material, especially a solid material or a suspension of a solid material in a liquid especially aqueous, medium.

According to a further aspect of the invention there is provided the use in a method of preparing a medicament for treatment of hyperphosphataemia of a metal sulphate material selected from at least one of calcium, lanthanum and cerium sulphate compounds treated with an alkali solution.

According to a still further aspect, there is provided a method of preparing a metal sulphate material, which method comprises treating a metal sulphate selected from at least one of calcium, lanthanum and cerium sulphate with an alkali solution.

BRIEF DESCRIPTION OF THE DRAWINGS

Preferred embodiments of the invention will now be described in more detail with reference to the following Examples (which also include comparative tests) and graphical representations. In each of FIGS. 1–8, the ordinate (y-axis) gives the percentage of phosphate bound and the abscissa (x-axis) the pH. In the Figures, In FIG. 1,

| | | | |
|---|---|---|---|
| ○ | Mg:Fe | 3:1 | prep 2 unaged |
| ● | Mg:Fe | 3:1 | prep 2 aged |
| Δ | Mg:Fe | 2:1 | prep 1 unaged |
| ▲ | Mg:Fe | 2:1 | prep 1 aged |
| ⊠ | Ca:Fe | 3:1 | unaged |
| ■ | Ca:Fe | 3:1 | aged |
| ☆ | Ca:Fe:Mg | | unaged |
| ★ | Ca:Fe:Mg | | aged |

Figure 2:
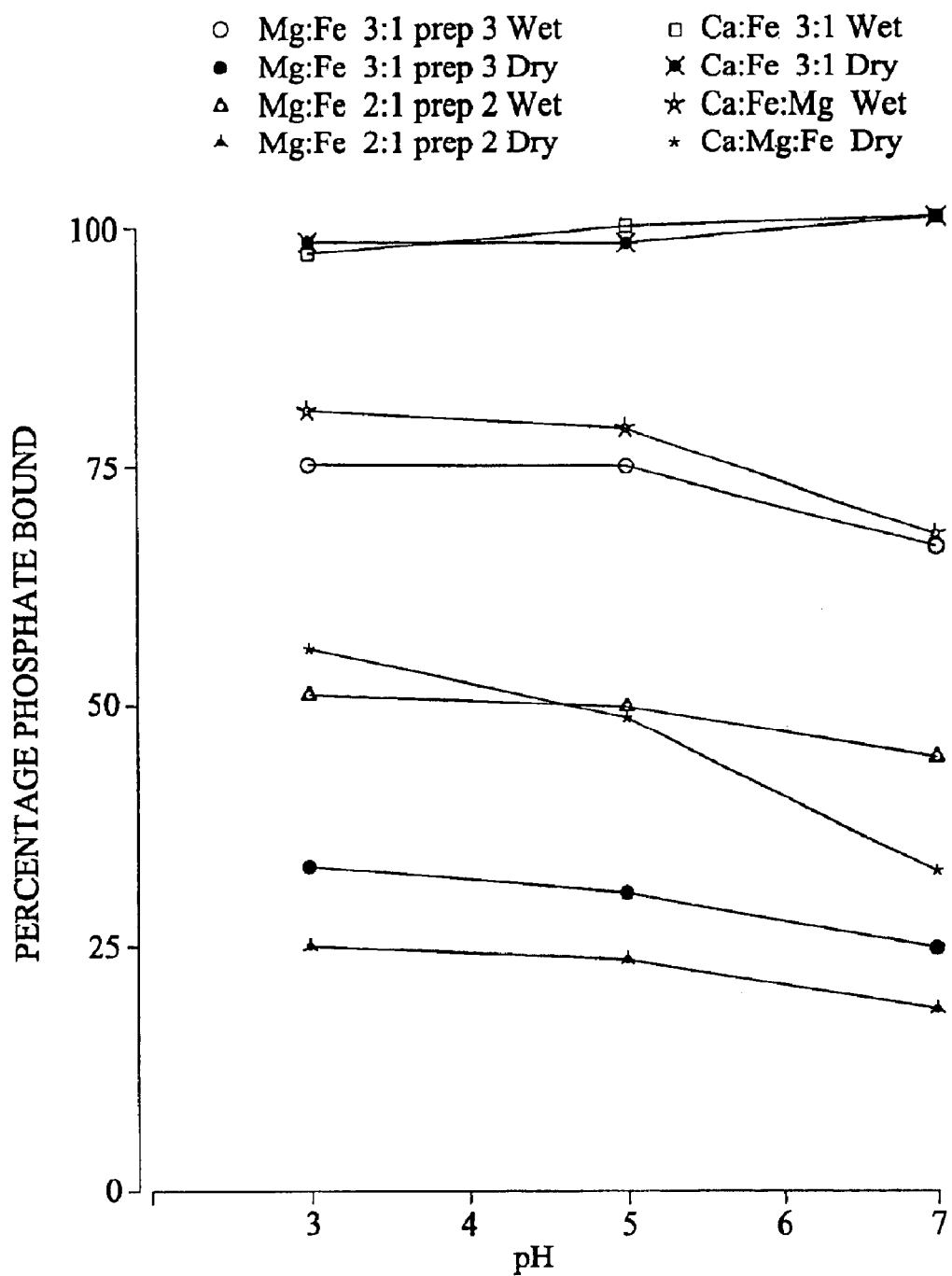

FIG. 2 shows the effect of pH and drying on percentage phosphate binding of mixed metal compounds. In FIG. 2,

| | | | |
|---|---|---|---|
| ○ | Mg:Fe | 3:1 | prep 3 wet |
| ● | Mg:Fe | 3:1 | prep 3 dry |
| Δ | Mg:Fe | 2:1 | prep 2 wet |
| ▲ | Mg:Fe | 3:1 | prep 2 dry |
| □ | Ca:Fe | 3:1 | wet |
| ■ | Ca:Fe | 3:1 | dry |
| ☆ | Ca:Fe:Mg | | wet |
| ★ | Ca:Mg:Fe | | dry |

Figure 3:
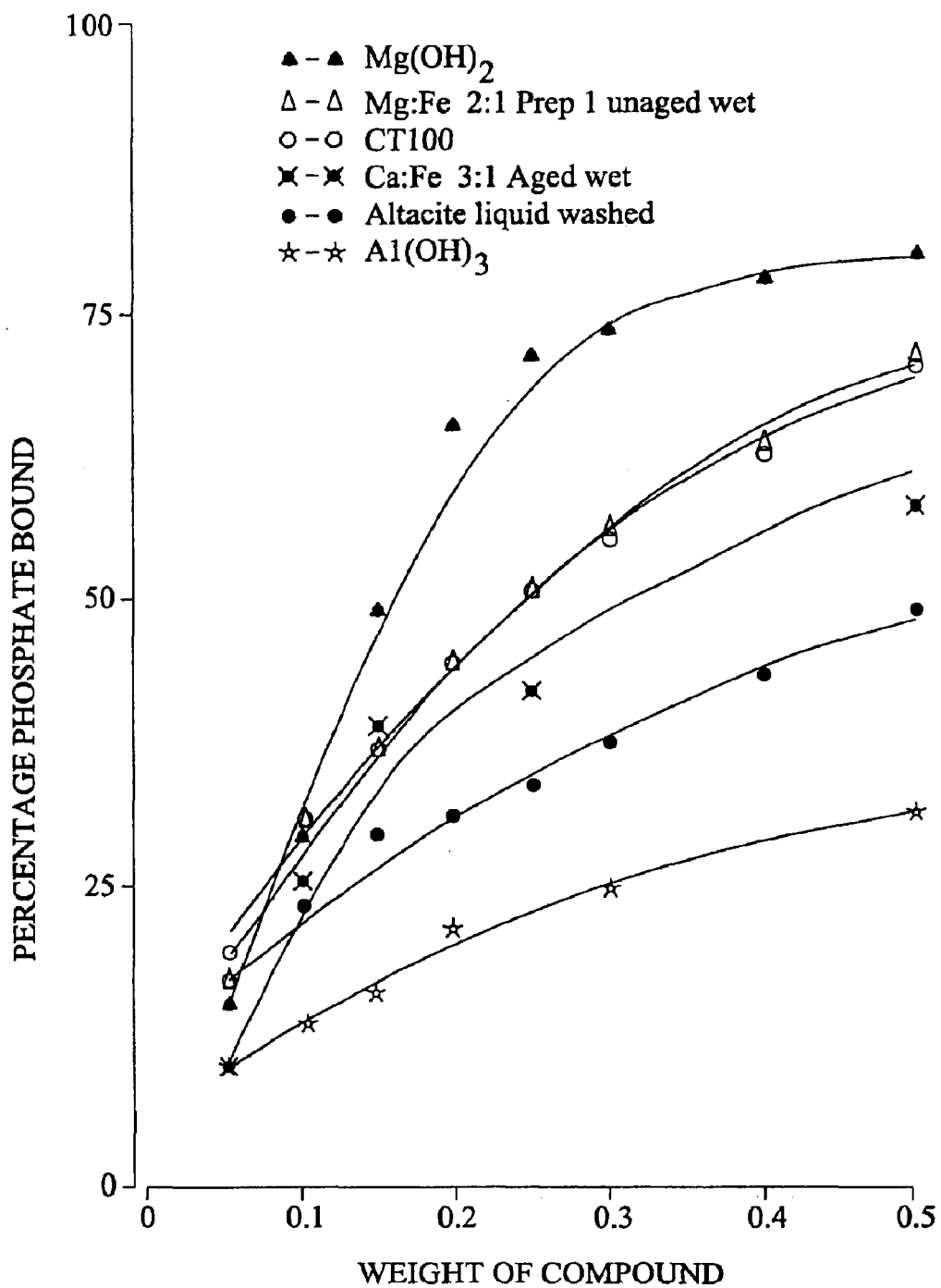

FIG. 3 shows the effect of increasing weight of compound on percentage phosphate bound at pH3. In FIG. 3,

| | | |
|---|---|---|
| ▲—▲ | Mg(OH)$_2$ | |
| Δ—Δ | Mg:Fe 2:1 | Prep unaged wet |
| ○—○ | CT100 | |
| ■—■ | CaFe 3:1 | Aged wet |
| ●—● | ALTACITE | liquid washed |
| *—* | Al(OH)$_3$ | |

Figure 4:
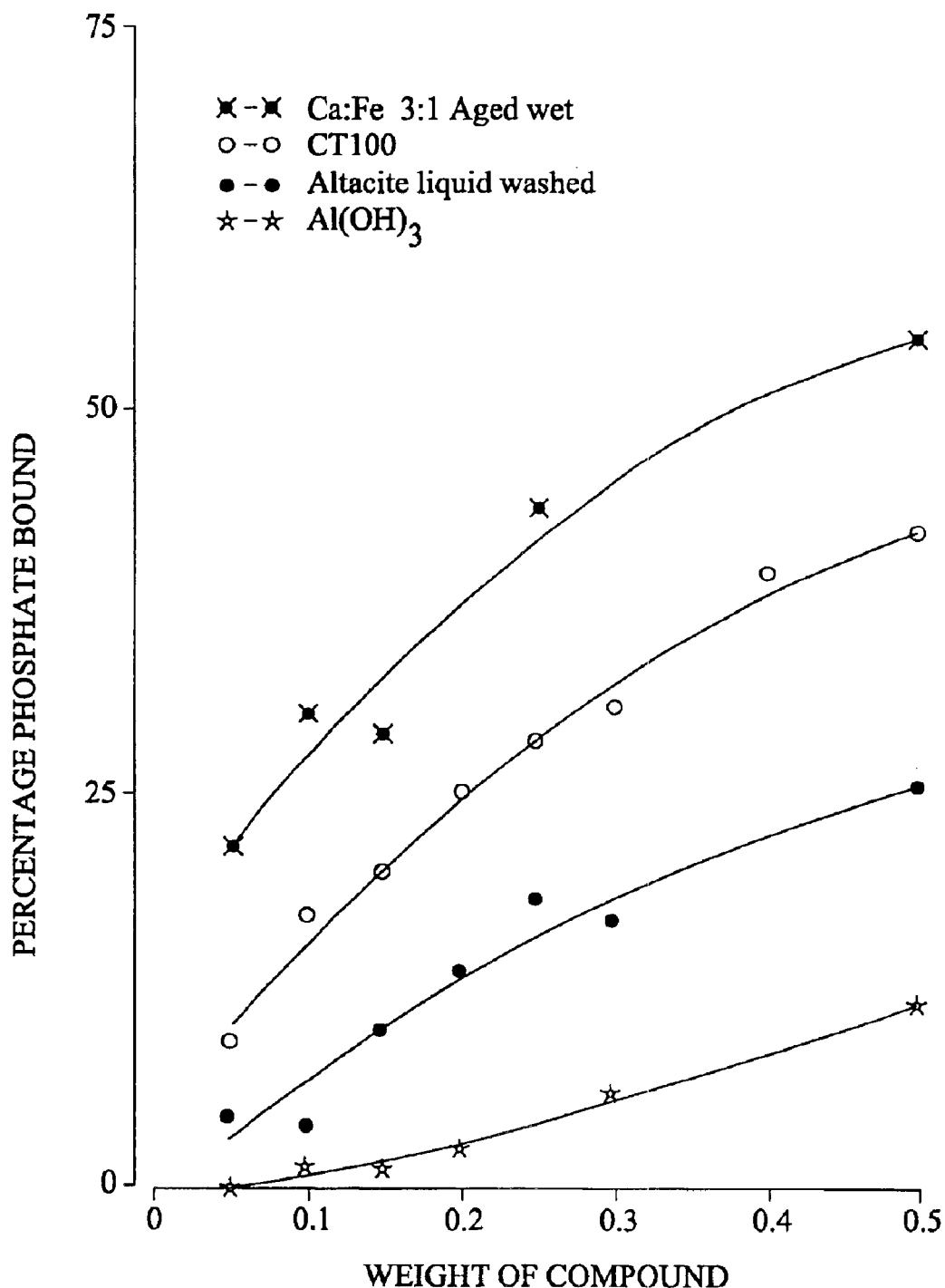

FIG. 4 shows the effect of increasing weight of compound on percentage phosphate bound at pH7. In FIG. 4,

| | | |
|---|---|---|
| ■—■ | CaFe 3:1 | Aged wet |
| ○—○ | CT100 | |
| ●—● | ALTACITE | liquid washed |
| *—* | Al(OH)$_3$ | |

Figure 5:
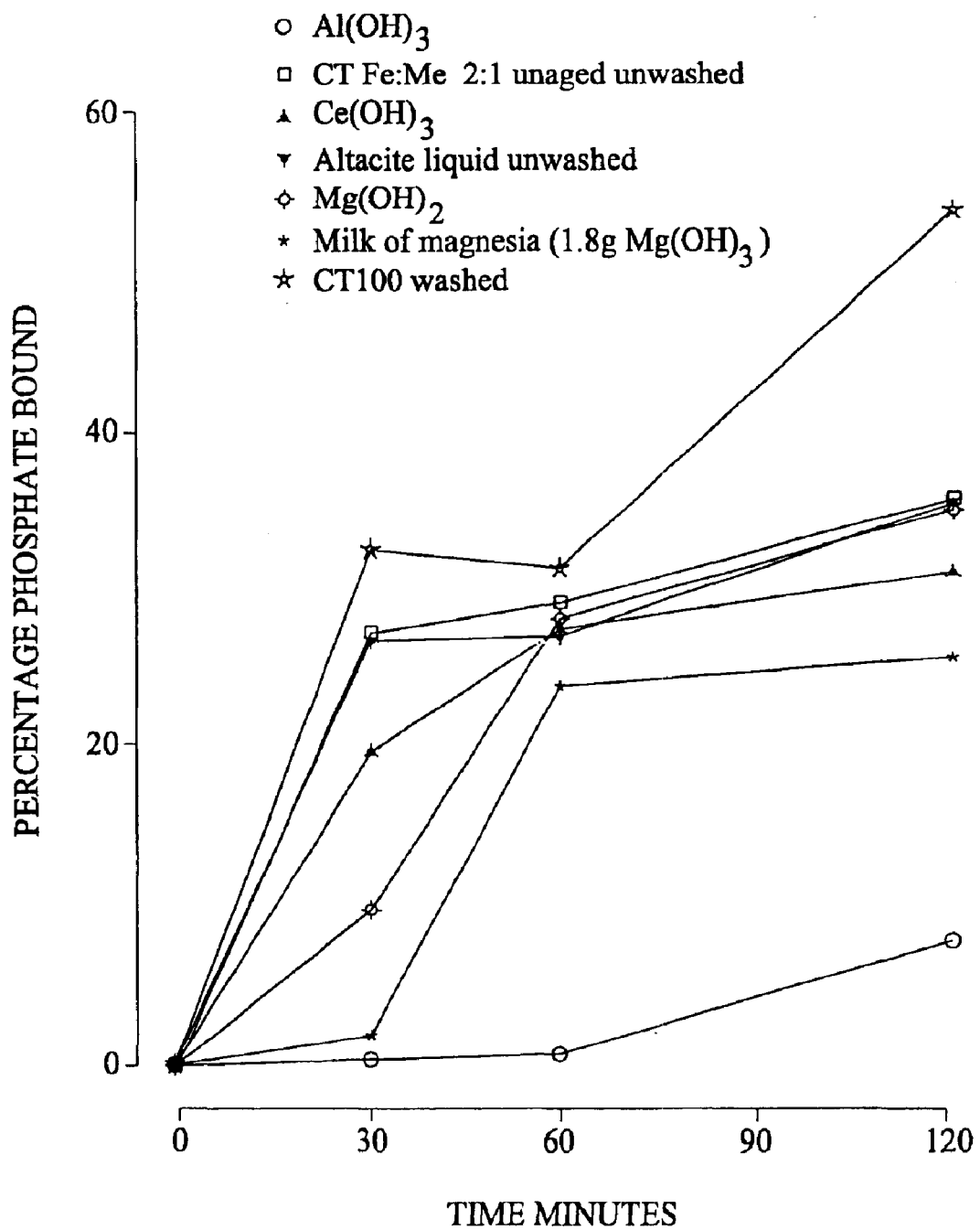

FIG. 5 shows the time course of phosphate binding in food. In FIG. 5,

| | | |
|---|---|---|
| ○ | Al(OH)$_3$ | |
| □ | CT Fe:Mg | 2:1 unaged washed |
| ▲ | Ce(OH)$_3$ | |
| ▼ | ALTACITE | liquid unwashed |
| ◇ | Mg(OH)$_2$ | |
| ☆ | Milk of Magnesia | (1.8 g Mg(OH)$_3$) |
| ★ | CT100 washed | |

Figure 6:
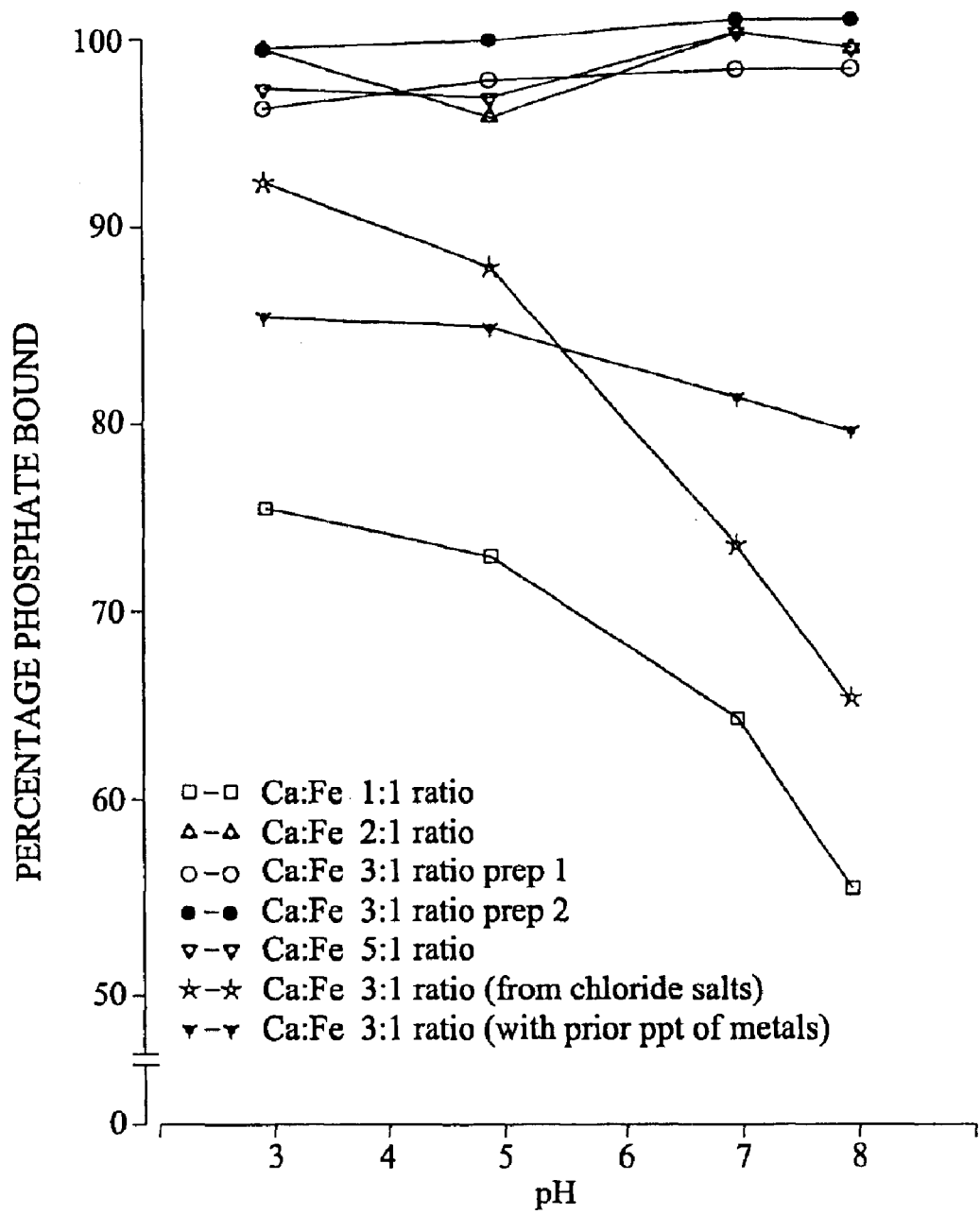

FIG. 6 shows the effect of phosphate binding by the calcium ferric iron preparations over the pH range 3–8. In FIG. 6,

| | | |
|---|---|---|
| □—□ | Ca:Fe | 1:1 ratio |
| Δ—Δ | Ca:Fe | 2:1 ratio |
| ○—○ | Ca:Fe | 3:1 ratio prep 1 |
| ●—● | Ca:Fe | 3:1 ratio prep 2 |
| ▽—▽ | Ca:Fe | 5:1 ratio |
| ★—★ | Ca:Fe | 3:1 ratio (from chloride salts) |
| ▼—▼ | Ca:Fe | 3:1 ratio (with prior ppt of metals) |

Figure 7:
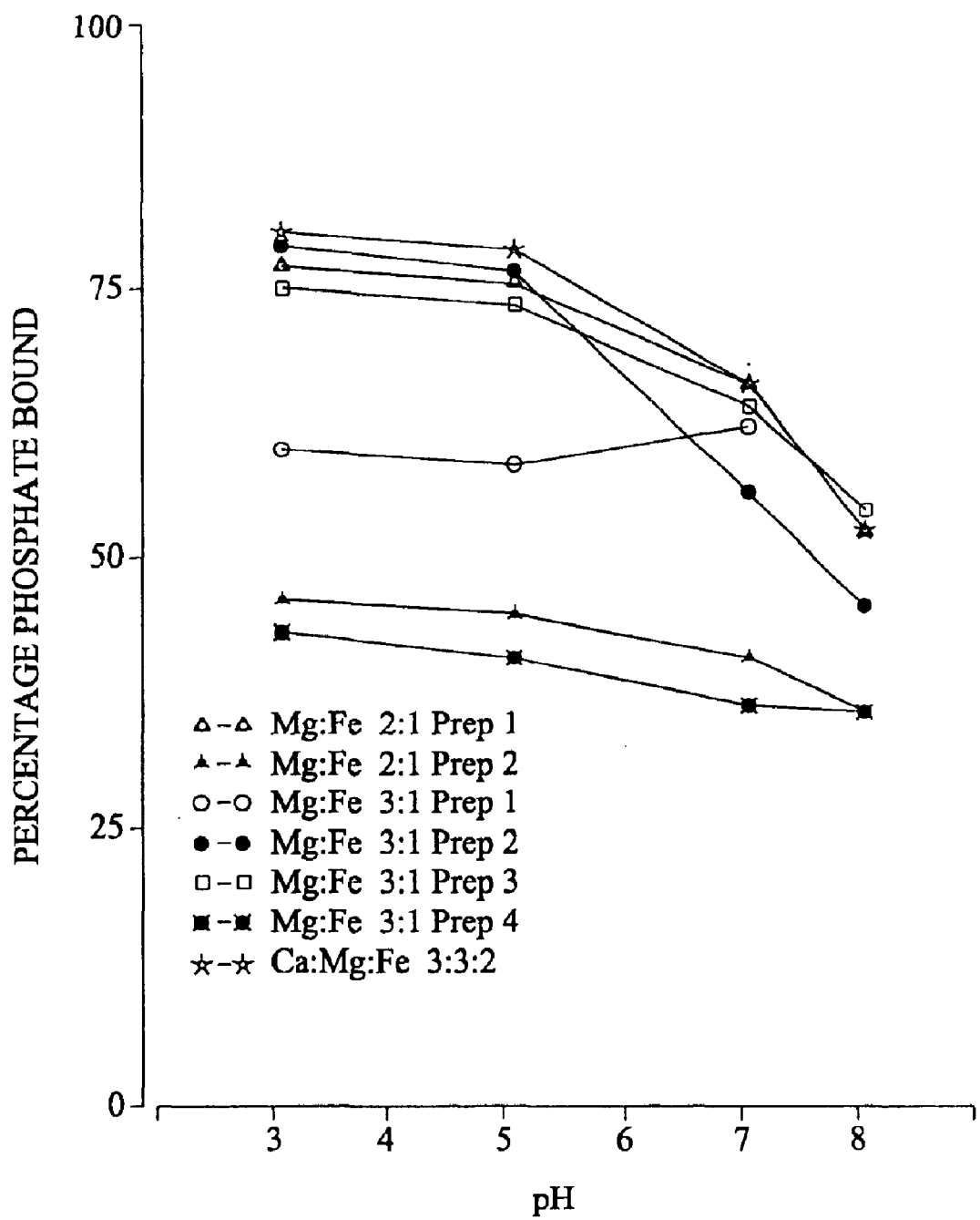

FIG. 7 shows the effect of phosphate binding by the magnesium ferric iron and calcium magnesium ferric iron preparations over the pH range 3–8. In FIG. 7,

| | | | |
|---|---|---|---|
| Δ—Δ | Mg:Fe | 2:1 | Prep 1 |
| ▲—▲ | Mg:Fe | 2:1 | Prep 2 |
| ○—○ | Mg:Fe | 3:1 | Prep 1 |
| ●—● | Mg:Fe | 3:1 | Prep 2 |
| □—□ | Mg:Fe | 3:1 | Prep 3 |
| ■—■ | Mg:Fe | 3:1 | Prep 4 |
| ★—★ | Ca:Mg:Fe | 3:3:2 | |

Figure 8:
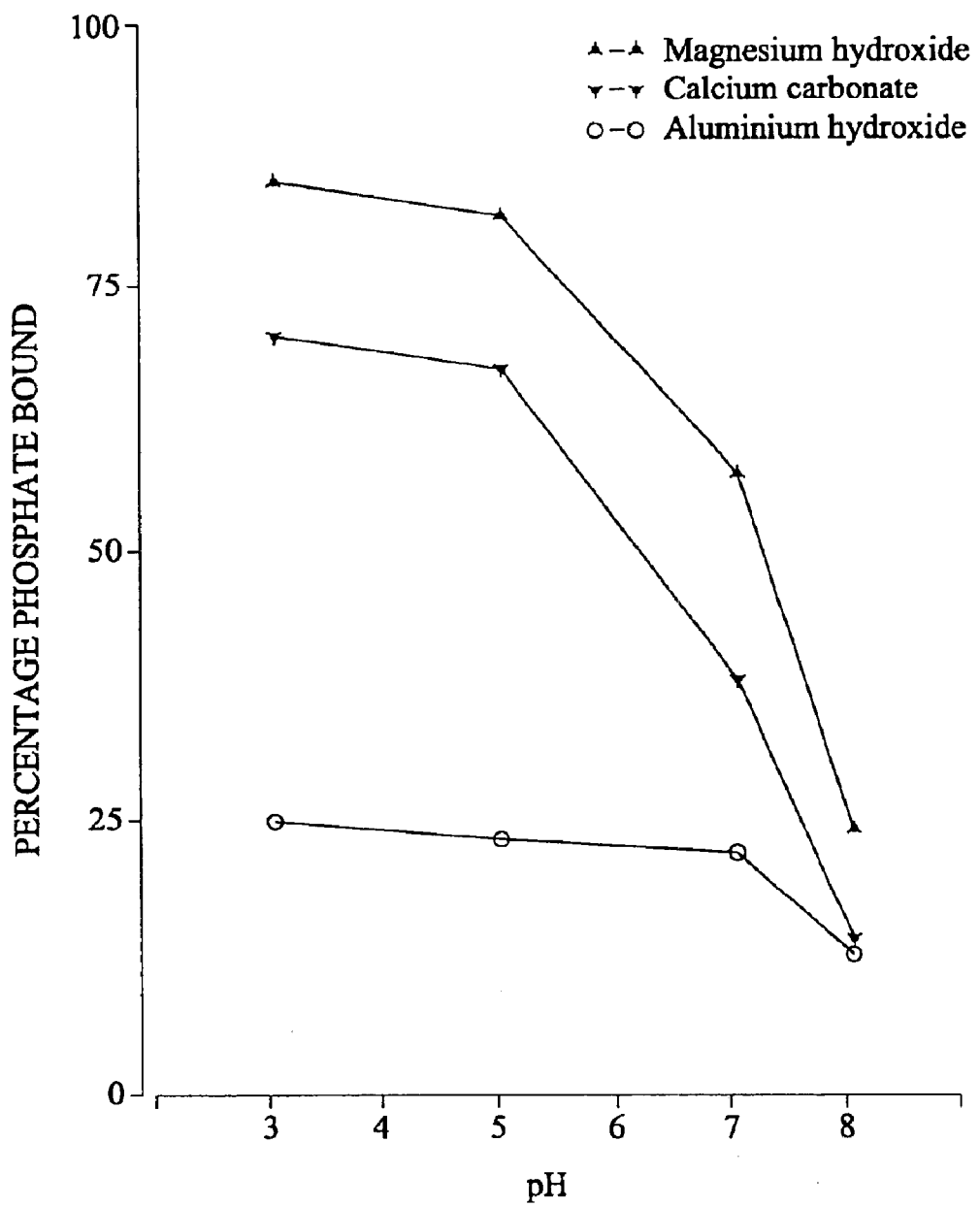

FIG. 8 shows the effect of phosphate binding by aluminium hydroxide, magnesium hydroxide and calcium carbonate over the pH range 3–8. In FIG. 8,

| | |
|---|---|
| ▲—▲ | Magnesium hydroxide |
| ▼—▼ | Calcium carbonate |
| ○—○ | Aluminium hydroxide |

Figure 10:
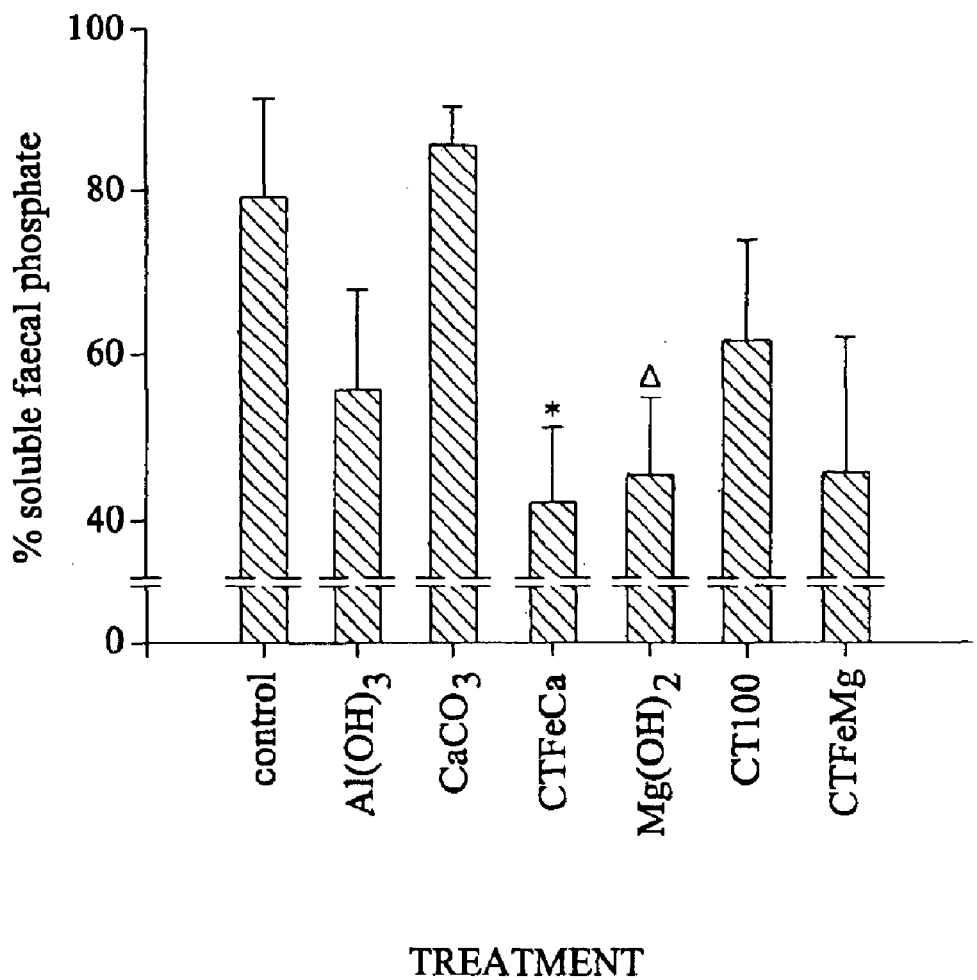

FIG. 9 shows the individual and mean (±1SEM) urinary phosphate excretion for control rats and those treated with phosphate binding compounds. In particular in FIG. 9, individual values of urinary phosphate excretion ($\mu$mol/24 hours) were plotted for controls (Δ) and animals treated with Al(OH)$_3$ (■), CaCO$_3$ (□), CTFeCa (●), Mg(OH)$_2$ (○), CT100 (◆) and CTFeMg (◇). Mean (±SEM) for each group are presented by points with error bars. *$p<0.05$ compared to Al(OH)$_3$ treated animal groups; and FIG. 10 shows the mean (±1SEM) soluble faecal phosphate (g$^{-1}$ dry weight) as a percentage of total (soluble and unsoluble) faecal phosphate (g$^{-1}$ dry weight) for control rats and those treated with phosphate binding compounds. In FIG. 10,

*$p<0.05$ compared to control and CaCO$_3$ treated animals

Δ$p<0.05$ compared to CaCO$_3$ treated animals

EXAMPLE 1

Preliminary Investigation

Compounds listed in Table 1 below, known to be effective phosphate binders were selected for investigation. In Table 1, the values indicate respective percentage phosphate binding capacity at each of pH3, pH7 and pH8, n indicating the number of trials made for each compound. In the Table, CT100 is a hydrotalcite of the formula Al$_2$Mg$_6$OH$_{16}$.CO$_3$.4H$_2$O, commercially available from Crosfield Limited (UK)and CT2000 is the compound CT100 in the form of an undried slurry.

The phosphate binding capacity was measured by mixing 3.2 mmol of the compound with 25 ml of 20 mmol l$^{-1}$ phosphate buffer for 30 min at 25° C. For all compounds except CT2000, which compounds were dry powders, the compounds were merely weighed and dosed. For CT2000, the slurry was dosed in an amount such as to give an equivalent of 1 g of a powder dried to constant weight at 40° C. Sodium phosphate and sodium hydrogen phosphate were mixed to provide respective phosphate solutions at pH3, 7 and 8 (HCl being added to provide pH3). The binder was separated from the solution by centrifugation (5 min, 3000 rpm) and filtration through 0.22 μm filters, to provide a supernatant, the phosphate content of which was then measured using a 911 Hitachi autoanalyser with Boehringer Mannhiem chemistry. The results are shown in Table 1, in which n refers to the number of observations and the values as the % of phosphate precipitated out of solution, calculated as follows:

100−[(x/y). 100]

where x=mmol phosphate in solution after precipitation; and
y=mmol phosphate in solution without precipitation.

TABLE 1

| Compound | pH 3 | pH 7 | pH 8 |
|---|---|---|---|
| Al(OH)$_3$ (n = 4) | 14.7 ± 1.8 | 6.2 ± 0.4 | 2.7 ± 1.6 |
| CaCO$_3$ (n = 4) | 15.3 ± 0.5 | 9.7 ± 1.8 | 2.4 ± 1.8 |
| Mg(OH)$_2$ (n = 4) | 61.1 ± 7.5 | 45.7 ± 5.9 | 12.5 ± 3.7 |
| Ce(OH)$_3$ (n = 3) | 69.8 ± 7.5 | 57.8 ± 8.9 | 60.5 ± 1.5 |
| CT100 (n = 3) | 94.6 ± 1.6 | 91.5 ± 2.5 | 91.7 ± 0.3 |
| CT2000 (n = 3) | 90.7 ± 1.2 | 87.2 ± 0.0 | 82.3 ± 1.4 |

As can be seen from Table 1, each of the hydrotalcite-like materials had a considerably higher phosphate binding capacity over a wider pH range.

Dosage relationship curves for the CT compounds and Al(OH)$_3$ in pH3, 5 and 7 phosphate buffer showed that the CT compounds bound at least twice as much phosphate as an equivalent weight of Al(OH)$_3$.

Al(OH)$_3$ released as much as 20,000–41,000 μg l$^{-1}$ of Al$^{3+}$. Moreover, although the CT compounds released a considerably lower amount (17–66 μg l$^{-1}$), this would still be likely to provide adverse effects in long time-dosage regimes.

Nevertheless, as indicated by Ookubu (supra); it was still thought necessary to include Al$^{3+}$ within the structure of a phosphate binding compound. However, in a test similar to that described above, it was found surprisingly that a compound prepared in a manner similar to that used for preparing CT100 (see Example 3 below) but substituting an equivalent amount of Fe$^{3+}$ gave an excellent phosphate binding capacity, especially at pH3 where a −70% phosphate binding capacity was achieved, without the risk of release of any aluminium.

EXAMPLE 2

Comparison of Mixed Metal Hydroxy Carbonates

Compounds tested:

(1) a hydroxy carbonate containing a 2:1 ratio Mg:Fe
(2) a hydroxy carbonate containing a 3:1 ratio of Mg:Fe
(3) a hydroxy carbonate containing a 3:1 ratio of Ca:Fe
(4) a hydroxy carbonate containing a 3:3:2 ratio of Ca:Mg:Fe
(5) CT100, a hydrotalcite of the formula Al2Mg6(OH)16CO3.4H2O
(6) ALTACITE, a hydrotalcite of the same formula as CT 100, commercially available from Roussell, in the form of an aqueous slurry
(7) magnesium hydroxide
(8) aluminum hydroxide.

Methods of Measuring Phosphate Binding Capacity

As indicated below, the following methods of measuring phosphate binding capacity were adopted:

Method 1—1 gram of each phosphate binder compound (taking hydration of the wet cake compound into account) was added to 25 ml, 40 mmol l$^{-1}$ sodium phosphate buffer adjusted to pH 3, pH 5 or pH 7 as described in Example 3 below. Samples were whirl mixed to ensure homogeneity and gently agitated at room temperature for 30 minutes. Following centrifugation for 5 min at 3000 rpm, the supernatant was filtered through 0.22 μm millipore filters. Soluble phosphate was measured in the supernatant. The percentage phosphate bound by the hydrotalcite was calculated.

Method 2—As method 1 but using 20 mmol l$^{-1}$ phosphate buffer.

Method 3—Milk (250 ml), cornflakes (50 g), bread (2 slices) and MARMITE (yeast extract) (5 g) were mixed in a stomacher for 30 minutes containing 0.01 M HCl (so as to simulate the conditions in the stomach). A 20 ml aliquot of food was removed and centrifuged. Phosphate was measured in the supernatant. Two grams of the phosphate binder compound was added to the bulk food slurry and mixed for a further 30 minutes. J an aliquot of food was taken and the phosphate measured in the supernatant following centrifugation. Further aliquots were taken after a further 30 and 90 minutes mixing.

In each of the above methods, for each of the compounds (1–(4), where a dry powder was dosed as the phosphate binder, phosphate binding was measured for a given dosage measured after drying to constant weight at 40° C. Where a wet cake was dosed (or ALTACITE (6) added), an amount equivalent to a given constant dry weight at 40° C. was used. For known commercially available binders, a given weight of the material supplied was used.

Results

Experiment 1: Effect of pH and Ageing on Percentage Phosphate Binding of Mixed Metal Compounds Phosphate binding compounds were prepared in the form of a wet slurry. Unaged samples were obtained by filtering and washing the wet slurry to form a wet cake which was tested in this form, while aged samples were obtained by heating the wet slurry to 80° C. for two hours prior to filtering of the cake, which was then tested. The percentage phosphate binding of the compounds when used aged or unaged across the pH range 3–7 was investigated in this manner.

Figure 1:
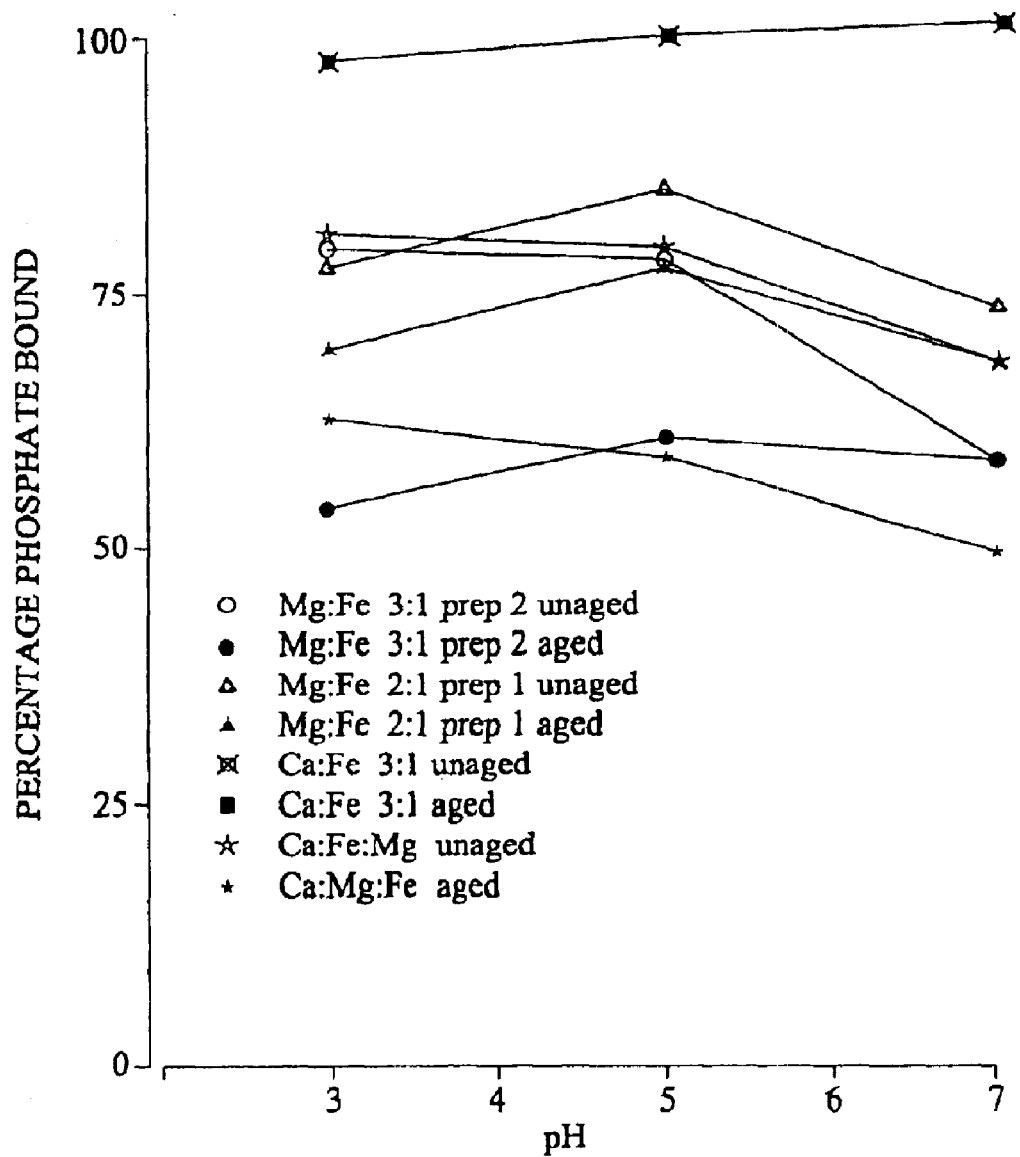
FIG. 1 shows the effect of pH and ageing on percentage phosphate binding of mixed metal compounds.

Method 1 was used for measuring phosphate binding capacity. The results are shown in FIG. 1.

The Ca:Fe 3:1 compound (3) bound almost 100% of the phosphate independently of pH. There was no difference between the aged and unaged compound.

The Mg:Fe compounds (1) and (2) in a 2:1 (prep 1) and 3:1 (prep 2) ratio respectively bound phosphate independently of pH over the range 3–7. The unaged compounds were better phosphate binders than the aged compounds at pH 3–7.

The Ca:Mg:Fe compound (3) also bound phosphate independently of pH; again the unaged was better than the aged compound.

Experiment 2: Effect of pH and Drying on Percentage Phosphate Binding of Mixed Metal Compounds The percentage phosphate binding of the compounds when used in the dry powder or wet (cake) form across the pH range 3–7 was investigated.

Method 1 was used for measuring phosphate binding capacity. The results are shown in FIG. 2.

Unaged compounds were compared in their wet (cake) form or following drying to constant weight. One gram weight of each compound was used for comparison (hydration of the wet (cake) compound was accounted for e.g. if the hydrotalcite was 20% dry weight (calculated on a constant dry weight at 40° C.), 5 grams were used).

In all cases, except the Ca:Fe 3:1 compound (3), where there was no difference, the wet (cake) form of the compound was a better phosphate binder than the dry powder form. Whether in the wet or dry form, all of the compounds (1)–(4) bound phosphate independently of pH. Similar results are obtained when using aged compounds in that the wet compound bound more phosphate than the dry powder compound.

Experiment 3: Effect of Increasing Amount of Phosphate Binder Compound on Percentage Phosphate Binding for Various Compounds at pH 3

Method 2 was used for measuring phosphate binding capacity. The results are shown in FIG. 3.

At pH 3, $Mg(OH)_2$, compound (7), was the best phosphate binder. Other studies have however showed this binding is pH dependent, binding almost no phosphate at pH 8. It would therefore have limited use in vivo.

The compounds Mg:Fe 2:1 (1), Ca:Fe 3:1(2) and CT100 (5) all bound up to 60–70% of the phosphate. Interestingly, the CT100 bound ~50% more phosphate at any weight than the ALTACITE (6), despite an identical molecular formulae.

$Al(OH)_3$ the phosphate binder often used to control serum phosphate levels was relatively ineffective at the range of weights tested.

Experiment 4: Effect of Increasing Amount of Phosphate Binder Compound on Percentage Phosphate Binding for Various Binders at pH 7

Method 2 was used for measuring phosphate binding capacity. The results are shown in FIG. 4.

At pH 7, the Mg:Fe 3:1 compound (2) was the best phosphate binder over the range of weights studied. The CT100 (5) bound at least twice as much phosphate than the ALTACITE (6) at any weight studied.

Experiment 5: Phosphate Binding in Food

Method 3 was used for measuring phosphate binding capacity. The results are shown in FIG. 5.

The results show that in food, the CT100 (5) was the best phosphate binder, followed by the Fe:Mg 2:1 compound (2). Again, aluminium hydroxide (8) was ineffective. Interestingly, magnesium hydroxide (7), the best phosphate binder at pH 3, is not the best when used in food. This is probably due to the buffering effect of the food, the initial pH of the slurry being ~5. It therefore shows the pH dependency of using magnesium hydroxide as a phosphate binder.

SUMMARY

Overall, the results demonstrated:

The Mg:Fe and Ca:Fe compounds (1)–(4) were efficient phosphate binders across a range of pH's likely to be found in the gastrointestinal tract.

Phosphate binding by the MgFe and MgCaFe compounds (1), (2) and (4) but not the CaFe compound (3) was reduced by ageing the compounds.

Drying the MgFe and MgCaFe compounds (1), (2) and (4) but not the CaFe compound (3) reduced their phosphate binding.

The known hydrotalcite compound CT100 (5) bound phosphate in food in vitro studies. It also reduced urinary phosphate excretion when given in vivo to normal individuals. However, as the new compounds (1)–(4) bound phosphate in water at least as well as CT100 (5) and a number of times better than $Al(OH)_3$ (8), we would expect they would also bind phosphate in vivo. These compounds have the added benefit of not releasing aluminium.

These new compounds (1)–(4) have a therapeutic potential in the control of serum phosphate levels in patients with end stage renal failure.

EXAMPLE 3

Further Investigations of Phosphate Binding Capacity

Method of Preparation and Measurement

In the following experiments, all chemicals were GPR grade, obtained from BDH. Millipore filters were obtained from Amicon, High Wycombe.

M1. Production of Metal Co-precipitate Preparations

All preparations were synthesised using the following method which, for a 3:1 ratio of $Mg^{2+}:Al^{3+}$ as respective cations $M^{2+}:M^{3+}$, resulted in the production of the hydrotalcite $Al_2Mg_6(OH)_{16}.CO_3 4H_2O$.

Use of calcium or magnesium as the $M^{2+}$ cation and ferric iron as the $M^{3+}$ cation allowed variations on the above theme to be achieved. By changing the ratio of the $M^{2+}:M^{3+}$ cations to 1:1, 2:1, 3:1 and 5:1, different composition materials could be produced. All compounds however had $CO_3^{2-}$ as the exchangeable anion.

For a 3:1 $M^{2+}:M^{3+}$ ratio, salt containing 2 moles of $M^{3+}$ and salt containing 6 moles of $M^{2+}$ were dissolved in 4 liters de-ionised water. In a separate 4 liters, 16 moles NaOH and 5 moles $Na_2CO_3$ were dissolved. Both solutions were pumped using peristaltic pumps into a flask with an overflow at ~2 liters and constantly mixed. The rate of addition of the solutions was such that the mixed solution had a pH of 10.0–10.5. After discarding the first litre, by which time a steady state had been established, 3–4 liters of overflowing slurry was collected. This was then vacuum filtered using a Buchner, washed with de-ionised water and re-filtered leaving a wet 'cake'.

Preparation names and the solution/suspension compositions used for their production are shown in Table 2. Due to the insolubility of calcium sulphate, when used as the $M^{2+}$ salt, constant stirring was necessary to prevent settling.

M2. Production of a Metal Precipitate Mixture

The metals in the solutions/suspensions described in Table 2 were precipitated at the same time by the addition of sodium hydroxide. A preparation was also made by precipitating the calcium and iron separately with sodium hydroxide, the precipitates were then mixed. For this, $Fe_2(SO_4)_3$ (1 mole) and NaOH(6 moles) were mixed in 4 litres deionised $H_2O$. In a separate 4 litres of water, $CaSO_4$ (6 moles), NaOH (12 moles) and $Na_2CO_3$ (5 moles) were mixed. These two suspensions were then fed into the flask with an overflow at ~2 liters and constantly mixed.

It proved impossible to alter the rate of addition of the precipitate suspensions such that the mixture had a pH of 10.0–10.5. The pH of the mixture fluctuated between ~11.5 and 12.5. After discarding the first liter, 3–4 liters of overflowing slurry was collected. This was then vacuum filtered using a Buchner, washed with de-ionised water and re-filtered leaving a wet 'cake'.

M3. Measurement of metal composition

Preparations were washed and dried to constant dry weight in an oven at ~40° C. One gram was titrated against 1M HCl until a constant pH of 1 was attained. The concentrations of $M^{2+}$ and $M^{3+}$ ions in solution were measured. For iron and calcium a Hitachi 911 autoanalyser with Boehringer Mannheim chemistry was used, while for magnesium a flame photometric atomic absorption spectroscopy was employed.

NB. Although the methods of analysis adopted here were of high accuracy, the method of sampling was such as to provide only an initial approximate assessment of the actual composition; in the results given below, compare the ratios predicted from the proportions of starting materials (assuming 100% yield) with those of the final preparations measured in this manner.

M4. Measurement of Phosphate Binding

Phosphate binding for the compounds prepared above, when dosed as a dry powder, was measured in each case at a dosage of 1.0 gram dry weight (determined by drying to constant weight at 40° C.). Where a wet cake was dosed, an amount equivalent to a 1 g dry weight was added. Phosphate binding of the conventional binders, magnesium hydroxide, aluminium hydroxide and calcium carbonate was also measured, in these cases using 1 g of material as supplied.

Phosphate binding capacity was determined over a pH range 3–8, approximately the range of pH's found in the normal gastrointestinal tract. 40 mmol $1^{-1}$ sodium phosphate buffers at pH 5, pH 7 and pH 8 were produced by mixing appropriate volumes of 40 mmol $1^{-1}$ $Na_2HPO_4$ and 40 mmol $1^{-1}$ $NaH_2PO_4$ solutions. A pH 3 phosphate solution was produced by addition of 1 M HCl to a 40 mmol $1^{-1}$ $NaH_2PO_4$ solution.

Preparations were suspended in 25 ml 40 mmol $1^{-1}$ phosphate buffer and whirl mixed to ensure homogeneity. This suspension was then gently agitated at room temperature for 30 minutes followed by centrifugation at 3000 rpm for 5 min. Following filtration of the supernatant through 0.22 μm millipore filters, soluble phosphate was measured using a 911 Hitachi autoanalyser with Boehringer Mannheim chemistry.

Phosphate bound was calculated as a percentage of that present in the original solution.

The compositions of solutions used to produce the metal co-precipitate preparations are shown in Table 2 below.

TABLE 2

Composition of solutions used to produce the metal co-precipitate preparations

| Material name | Moles $M^{2+}$ salt | Moles $M^{3+}$ salt | Moles NaOH | Moles $Na_2CO_3$ |
|---|---|---|---|---|
| Mg:Fe 2:1 (Prep 1) | 4 Mole $MgSO_4$ | 1 Mole $Fe_2(SO_4)_3$ | 12 | 5 |
| Mg:Fe 2:1 (Prep 2) | 4 Mole $MgSO_4$ | 1 Mole $Fe_2(SO_4)_3$ | 12 | 5 |
| Mg:Fe 3:1 (Prep 1) | 6 Mole $MgSO_4$ | 1 Mole $Fe_2(SO_4)_3$ | 16 | 5 |
| Mg:Fe 3:1 (Prep 2) | 6 Mole $MgSO_4$ | 1 Mole $Fe_2(SO_4)_3$ | 16 | 5 |
| Mg:Fe 3:1 (Prep 3) | 6 Mole $MgSO_4$ | 1 Mole $Fe_2(SO_4)_3$ | 16 | 5 |
| Mg:Fe 3:1 (Prep 4) | 6 Mole $MgSO_4$ | 1 Mole $Fe_2(SO_4)_3$ | 16 | 5 |
| Ca:Fe 1:1 | 2 Mole $CaSO_4$ | 1 Mole $Fe_2(SO_4)_3$ | 8 | 5 |
| Ca:Fe 2:1 | 4 Mole $CaSO_4$ | 1 Mole $Fe_2(SO_4)_3$ | 12 | 5 |
| Ca:Fe 3:1 (Prep 1) | 6 Mole $CaSO_4$ | 1 Mole $Fe_2(SO_4)_3$ | 16 | 5 |
| Ca:Fe 3:1 (Prep 2) | 6 Mole $CaSO_4$ | 1 Mole $Fe_2(SO_4)_3$ | 16 | 5 |
| Ca:Fe 5:1 | 10 Mole $CaSO_4$ | 1 Mole $Fe_2(SO_4)_3$ | 24 | 5 |
| Ca:Fe 3:1 (made with chloride salts) | 6 Mole $CaCl_2$ | 2 Mole $FeCl_2$ | 16 | 5 |
| Ca:Mg:Fe 3:3:2 | 3 Mole $MgSO_4$ 3 Mole $CaSO_4$ | 1 Mole $Fe_2(SO_4)_3$ | 16 | 5 |

Results

The following results were obtained.

R1. Predicted and Measured Metal Compositions of the Preparations

To determine if the ratio of metal ions in the original solutions was also present in the end preparation, all materials were hydrolysed with 1M HCl and the solution metal ion concentrations measured. The results are shown in Table 3 below. These show that the compounds prepared as above were indeed mixed metal compounds.

TABLE 3

Predicted and measured metal compositions of the preparations

| Material name | Predicted $M^{2+}:M^{3+}$ ratio | Measured $M^{2+}:M^{3+}$ ratio |
|---|---|---|
| Mg:Fe 2:1 (Prep 2) | 2:1 | 1.7:1 |
| Mg:Fe 3:1 (Prep 1) | 2:1 | 2.4:1 |
| Mg:Fe 3:1 (Prep 2) | 3:1 | 2.2:1 |
| Mg:Fe 3:1 (Prep 3) | 3:1 | 2.2:1 |
| Mg:Fe 3:1 (Prep 4) | 3:1 | 2.3:1 |
| Ca:Fe 1:1 | 1:1 | 1.3:1 |
| Ca:Fe 2:1 | 2:1 | 1.6:1 |
| Ca:Fe 3:1 (Prep 2) | 3:1 | 2.6:1 |
| Ca:Fe 5:1 | 5:1 | 1.3:1 |
| Ca:Fe 3:1 (made with Cl- salts) | 3:1 | 1.4:1 |
| Ca:Fe 3:1 (mixing of metals after ppt$^n$) | 3:1 | 1.1:1 |
| Ca:Mg:Fe | 3:3:2 | 2.9:2.3:2 |

R2. Phosphate Binding

R2.1 Calcium and Ferric Iron Containing Preparations

The preparations containing different ratios of calcium to ferric iron were tested for their capacity to bind phosphate.

The reproducibility of results was demonstrated with reference to a predicted $Ca^{2+}:Fe^{3+}$ ratio of 3:1 and this is shown in Table 4 below, while the results obtained for different ratios are shown in FIG. 6 and Table 5 below.

In the graphs shown in FIG. 6, values plotted are the mean of the two separate experiments.

(i) A Predicted $Ca^{2+}:Fe^{3+}$ Ratio of 3:1

Two different calcium ferric iron preparations with a predicted 3:1 ratio were synthesised. When preparation 2 was hydrolysed, elemental analysis showed the measured calcium to ferric iron ratio to be 2.6:1. Insufficient sample of preparation 1 was available for hydrolysis.

Phosphate binding by each preparation was tested in two separate experiments across the pH range 3–8. Binding was reproducible for both preparations at each pH (Table 4). At least 96% of the phosphate present in solution was bound by each preparation at each pH (FIG. 5, Table 4).

TABLE 4

Reproducibility of phosphate binding for preparations with a predicted 3:1 $Ca^{2+}:Fe^{3+}$ ratio

| | Percentage phosphate binding at | | | |
|---|---|---|---|---|
| | pH 3 | pH 5 | pH 7 | pH 8 |
| Prep 1 (exp. 1) | 97 | 98 | 98 | 97 |
| Prep 1 (exp. 2) | 96 | 96 | 97 | 97 |
| Prep 2 (exp. 1) | 98 | 99 | 100 | 100 |
| Prep 2 (exp. 2) | 100 | 99 | 100 | 99 |

(ii) A Predicted $Ca^{2+}:Fe^{3+}$ Ratio of 1:1

One calcium ferric iron preparation with a predicted 1:1 ratio was synthesised. Elemental analysis of the hydrolysed material showed the measured calcium to ferric iron ratio to be 1.3:1.

Greater than 50% of the phosphate present in solution was bound by the preparation at pH 3–8 (FIG. 6, Table 5). Phosphate binding was pH dependent. The material bound 28% less phosphate at pH 8 than at pH 3.

(iii) A Predicted $Ca^{2+}:Fe^{3+}$ Ratio of 2:1

One calcium ferric iron preparation with a predicted 2:1 ratio was synthesised. Elemental analysis of the hydrolysed material showed the measured calcium to ferric iron ratio to be 1.6:1.

At least 97% of the phosphate present in solution was bound over the pH range 3–8 (FIG. 6, Table 5). There was no pH dependency of the binding.

(iv) A Predicted $Ca^{2+}:Fe^{3+}$ ratio of 5:1

One calcium ferric iron preparation with a predicted 5:1 ratio was synthesised. Elemental analysis of the hydrolysed material showed the measured calcium to ferric iron ratio to be 1.5:1.

At least 95% of the phosphate present in solution was bound over the range pH 3–8 (FIG. 6, Table 5). There was no pH dependency of the binding.

(v) A Predicted $Ca^{3+}:Fe^{2+}$ Ratio of 3:1 Made Using Metal Chloride Salts

Due to the insolubility of calcium sulphate, a preparation was made using the soluble salt, calcium chloride. One calcium ferric iron preparation with a predicted 3:1 ratio was synthesised. Elemental analysis of the hydrolysed material showed the measured calcium to ferric iron ratio to be 1.4:1.

Greater than 60% of the phosphate present in solution was bound over the pH range 3–8 (FIG. 6, Table 5). Phosphate binding was pH dependent with 31% less precipitated at pH 8 than pH 3.

(vi) A Predicted $Ca^{2+}:Fe^{3+}$ Ratio of 3:1 Made by Precipitating the Calcium and Iron Prior to Mixing A preparation was made to determine whether precipitation of calcium and ferric iron from their sulphates prior to mixing would produce a phosphate binding material. This compound was prepared as in methods M2. The predicted ratio of calcium to ferric iron was 3:1 although, the ratio measured following acid hydrolysis was 1.1:1.

Greater than 75% of the phosphate present in solution was bound over the pH range 3–8 (FIG. 6, Table 5). The binding was pH dependent to a small degree, at pH 8, 8% less phosphate was bound than at pH 3.

TABLE 5

Phosphate binding by the calcium ferric containing preparations at pH 3–8

| Predicted | Percentage phosphate bound | | | |
|---|---|---|---|---|
| $Ca^{2+}:Fe^{3+}$ ratio | pH 3 | pH 5 | pH 7 | pH 8 |
| 1:1 | 75 | 72 | 63 | 54 |
| 2:1 | 99 | 95 | 99 | 98 |
| 3:1* | 98 | 99 | 100 | 100 |
| 5:1 | 97 | 96 | 99 | 98 |
| 3:1 (made with chloride salts) | 92 | 87 | 72 | 64 |
| 3:1 (with prior ppt$^n$ of metals) | 85 | 84 | 80 | 78 |

*Preparation 2 (exp. 1) of Table 4 also included for comparison

R2.2 Preparations Containing Magnesium and Ferric Iron

A number of preparations containing different ratios of magnesium to ferric iron were tested for their ability to bind phosphate.

The reproducibility of results was demonstrated in each case and these results are shown in Tables 6–8 below, while a comparison of the results is shown in FIG. 7.

(i) A Predicted $Mg^{2+}:Fe^{3+}$ Ratio of 3:1

Four magnesium ferric iron preparations were synthesised with the predicted ratio of 3:1. Preparation 1 had an actual $Mg^{2+}:Fe^{3+}$ ratio of 2.4:1 Preparations 2, 3 and 4 had measured $Mg^{2+}:Fe^{3+}$ ratios of 2.2:1, 2.2:1 and 2.3:1 respectively.

Preparation 1 bound at least 60% of the phosphate over the pH range 3–7. Preparations 2, 3 and 4 bound at least 40%, 50% and 30% of the phosphate respectively over the pH range 3–8 (FIG. 7, Table 6). Phosphate binding by preparation 4 was reproducible (Table 6). A shortage of material meant binding experiments on preparations 1, 2 and 3 were carried out once.

The three preparations studied over the pH range 3–8 all displayed pH dependency in their phosphate binding. Preparations 2 and 3 bound 44% and 29% less phosphate respectively at pH 8 than pH 3. Preparation 4 bound a mean of 21% less phosphate at pH 8 than pH 3.

TABLE 6

Phosphate binding for preparations with the predicted 3:1 $Mg^{2+}:Fe^{3+}$ ratio

| | Percentage phosphate binding at | | | |
|---|---|---|---|---|
| | pH 3 | pH 5 | pH 7 | pH 8 |
| Prep 1 | 60 | 58 | 61 | — |
| Prep 2 | 79 | 76 | 55 | 44 |
| Prep 3 | 75 | 73 | 63 | 53 |
| Prep 4 (exp. 1) | 41 | 40 | 34 | 37 |
| Prep 4 (exp. 2) | 45 | 39 | 36 | 32 |

(i) A Predicted $Mg^{2+}:Fe^{3+}$ Ratio of 2:1

Two magnesium ferric iron preparations with a predicted 2:1 ratio were synthesised. Elemental analysis of preparation 2 following hydrolysis showed the measured magnesium to ferric iron ratio to be 1.7:1. Insufficient sample was available to study the elemental composition of preparation 1.

Preparation 1 bound greater than 60% of the phosphate across the pH range 3–7. Preparation 2 reproducibly bound greater than 30% of the phosphate across the pH range 3–8

(Table 7, FIG. 7). This was pH dependent with a mean of 27% less phosphate being bound at pH 8 than pH 3.

TABLE 7

Phosphate binding for preparations with the predicted 2:1 $Mg^{2+}:Fe^{3+}$ ratio

| | percentage phosphate binding at | | | |
|---|---|---|---|---|
| | pH 3 | pH 5 | pH 7 | pH 8 |
| Prep 1 | 77 | 75 | 65 | — |
| Prep 2 (exp. 1) | 50 | 48 | 41 | 37 |
| Prep 2 (exp. 2) | 42 | 39 | 38 | 30 |

2.3 A Magnesium, Calcium and Ferric Iron Containing Preparation (i) A Predicted $Ca^{2+}:Mg^{2+}:Fe^{3+}$ Ratio of 3:3:2

One calcium magnesium ferric iron preparation with a predicted 3:3:2 ratio was synthesised. When this was hydrolysed, elemental analysis showed the measured calcium to magnesium to ferric iron ratio to be 2.9:2.3:2.

This compound bound greater than 45% of the phosphate in solution across the pH range 3–8 (FIG. 7). Two separate experiments showed that the phosphate binding was reproducible (Table 8). Binding was pH dependent with a mean of 36% less phosphate precipitated at pH 8 than pH3.

TABLE 8

Phosphate binding for preparation with a predicted 3:3:2 $Ca^{2+}:Mg^{2+}:Fe^{3+}$ ratio

| | Percentage phosphate binding at | | | |
|---|---|---|---|---|
| | pH 3 | pH 5 | pH 7 | pH 8 |
| exp. 1 | 80 | 77 | 65 | 54 |
| exp. 2 | 80 | 78 | 64 | 48 |

R2.4 Phosphate Binding By Conventional Compounds

The compounds aluminium hydroxide, magnesium hydroxide and calcium carbonate were also tested for their ability to bind phosphate. The method was as previously described in M4.

All compounds were tested twice and showed reproducible phosphate binding across the pH range studied and the results are shown in FIG. 8 and Table 9 below. In FIG. 8, values plotted are the mean of two separate experiments for each compound.

As can be seen, phosphate binding was pH dependent with a mean 2.4 fold increase in binding by $Al(OH)_3$ at pH 3 compared to pH 8. $Mg(OH)_2$ bound a mean 3.7 times more phosphate at pH 3 than pH 8. $CaCO_3$ bound a mean of 5.9 times more phosphate at pH 3 than pH 8.

TABLE 9

Phosphate binding by $Al(OH)_3$, $Mg(OH)_2$ and $CaCO_3$

| | Percentage phosphate binding at | | | |
|---|---|---|---|---|
| | pH 3 | pH 5 | pH 7 | pH 8 |
| $Al(OH)_3$ | 20 | 19 | 18 | 9 |
| $Al(OH)_3$ | 30 | 25 | 23 | 12 |
| $Mg(OH)_2$ | 81 | 82 | 54 | 17 |
| $Mg(OH)_2$ | 87 | 80 | 58 | 28 |
| $CaCO_3$ | 69 | 63 | 30 | 8 |
| $CaCO_3$ | 72 | 70 | 43 | 16 |

EXAMPLE 4

Calcium Sulphate as Phosphate Binder

The following compounds were tested as phosphate binders:

1. Anhydrous calcium sulphate treated with sodium hydroxide

2. Anhydrous calcium sulphate

3. $CaSO_4,2H_2O$.

4. Ferrous/ferric co-precipitate

5. Ferric precipitate

1. Anhydrous Calcium Sulphate Treated with Sodium Hydroxide

This was prepared by mixing anhydrous calcium sulphate ($CaSO_4$) (0.1 moles), with sodium hydroxide (NaOH) (0.2 moles) in 100 ml de-ionised water for 30 minutes at room temperature. The mixture was centrifuged for 2 min at 3000 rpm and the supernatant discarded. The residue was washed by mixing with 100 ml water for 5 minutes followed by centrifugation for 2 min at 3000 rpm. The supernatant was discarded and the washing procedure repeated a further three times. The resultant solid was heated to constant dry weight at 60° C.

2. Anhydrous Calcium Sulphate

A commercially available dry anhydrous calcium sulphate powder was used.

3. Calcium Sulphate Dihydrate

A commercially available calcium sulphate dihydrate powder was used.

4. Ferrous/ferric Co-precipitate

This was prepared by co-precipitating ferrous sulphate $FeSO_4$ and ferric sulphate $Fe_2(SO_4)_3$ with sodium hydroxide to obtain a hydrated iron oxide compound. The predicted $Fe^{2+}:Fe^{3+}$ ratio was 3:1.

5. Ferric Precipitate

This was prepared by mixing ferric sulphate ($Fe_2(SO_4)_3$) (0.1 moles), with sodium hydroxide (NaOH)(0.3 moles) in 100 ml de-ionised water for 30 minutes at room temperature.

The mixture was centrifuged for 5 min at 3000 rpm and the supernatant discarded.

The precipitate was washed by mixing with 100ml water for 5 minutes followed by centrifugation for 5 min at 3000 rpm. The supernatant was discarded and the washing procedure repeated a further 3 times.

The precipitate was heated to constant dry weight at 60° C.

Phosphate Binding

The phosphate binding capacity of each of the above materials was measured as described above in Example 3, using one gram of each compound in 25 ml phosphate solution 40 mmol $l^{-1}$, pH 3–8.

The results are shown in Table 10 below.

TABLE 10

Phosphate binding over the pH range 3–8 by alkali treated calcium sulphate, anhydrous and hydrated calcium sulphates and an $Fe^{2+}:Fe^{3+}$ compound with a predicted 3:1 ratio and an $Fe^{3+}$ compound

| Compound | Percentage phosphate bound at | | | |
|---|---|---|---|---|
|  | pH 3 | pH 5 | pH 7 | pH 8 |
| Treated $CaSO_4$ | 100 | 100 | 100 | 100 |
| Anhydrous $CaSO_4$ | 2 | 7 | 47 | 55 |
| $CaSO_4.2H_2O$ | 0 | 0 | 57 | 89 |
| $Fe^{2+}:Fe^{3+}$ 3:1 | 26 | 18 | 33 | — |
| $Fe^{3+}$ | 56 | 59 | 56 | 41 |

From the above, it can be seen firstly that mixed metal compounds preferably containing each of a ferric cations and at least one of magnesium, calcium, lanthanum and cerium cation, and at least one of hydroxyl and carbonate anions and optionally at least one of sulphate, chloride and oxide have excellent phosphate binding capacity at a buffer pH relevant to physiological conditions in the gastrointestinal tract.

In particular, they show excellent phosphate binding capacity over a pH range of from 2–8, especially 3–7, and are therefore able to bind phosphate both in the stomach region (upper tract) where the pH would normally be about 3–4, up to 7, possibly depending upon the pH of the binder itself, and also in the lower tract, for example in the duodenum or jejunum, where the pH is likely to be $\geq 7$.

In view of this high binding capacity, lower dosages are possible.

Moreover, for the same weight of phosphate binding compound a mixed calcium/ferric compound contains less ferric ion than the corresponding compound containing iron alone. This allows a small in vivo dosage of iron for at least the same phosphate binding capacity, thus raising the likely tolerance of a patent to the dosage given.

The phosphate binding capacity of the mixed magnesium/ferric compound, is also remarkably less pH dependent as compared with magnesium hydroxide. Moreover, the magnesium tends to be stabilised, leading to a lower expected release thereof when administered in vivo with expected reduced side effects such as hypermagnesaemia. Likewise, the iron tends to be stabilised, leading to a lower expected release thereof in vivo, with an expected reduction in the free radical formation in vivo often encountered with $Fe^{3+}$ ions, so leading to less damage of membrane tissue.

It is also found, particularly surprisingly, that the above also applies to calcium sulphate after treatment thereof with an alkali solution.

EXAMPLE 5

Mixed Metal Hydroxy Carbonate as Phosphate Binders—in Vivo Study in Rats

Materials and Methods

The following chemicals unless otherwise stated were GPR grade from BDH/Merck (Poole, UK): $CaSO_4$, $Fe_2(SO_4)_3.xH_2O$ (technical grade), $MgSO_4$, $CaCO_3$, NaOH, 70% Nitric acid (redistilled, 99.99% purity). $Al(OH)_3$ and $Mg(OH)_2$ were obtained from Sigma (Poole UK). CT100 was obtained from Crosfield Ltd (Warrington, UK).

Phosphate binders were incorporated into the standard rat diet rat/mouse maintenance No 1 food obtained from Lilico (Betchworth, Surrey UK).

Production of the CT Compounds

CTFeCa and CTFeMg were mixed metal hydroaltacites, having a predicted ratio of $Mg^{2+}$ or $Ca^{2+}:Fe^{3+}$ of 3:1, produced in the laboratory following a standard laboratory procedure for mixed metal hydroxy carbonate preparations as described in Example 3 (M2). This $metal^{2+}$ sulphate, 6 moles, and $metal^{3+}$ sulphate, 2 moles, were dissolved in 4 liters de-ionised $H_2O$. In a separate flask, 16 moles NaOH and 5 moles $Na_2CO_3$ were dissolved in 4 liters de-ionised $H_2O$. The two solutions were pumped using peristaltic pumps into a flask with an overflow at ~2 liters, the rate of addition of the solutions was such that when mixed, the resulting suspension had a pH of 10.0–10.5. After discarding the first liter, by which time a steady state had been established, 3–4 liters of overflowing slurry was collected. This was vacuum filtered using a Buchner flask and washed with 1 liter de-ionised water three times. To allow incorporation into rat food, the wet "cake" compound was dried to constant dry weight at 50° C. and ground with a mortar and pestle.

In vivo Studies in the Rat

Twenty eight rats (Sprague-Dawley strain), weight range 275–307 grams were divided into seven groups, each consisting of four animals (in Tables 11–14, n=4). The phosphate binders were incorporated into the rat food at a concentration of 1% (w/w). Each group of rats was fed a single diet ad libitum for seven days and had unlimited access to de-ionised water. Animals were then weighed and transferred to metabowls for 24 hours where they received 18 grams of the control diet and unlimited access to water. Total 24 hour urine and faecal output was collected during this time. At the end of the treatment periods, animals were reweighed and a blood sample was obtained via the carotid artery following anaesthetisation with sodium pentobarbitone (Sagatal) 0.1 ml/100 g body weight of a 60 mg/ml solution.

Preparation of Faeces and Urine

Due to the design of the metabowls, the rat faeces were unavoidably contaminated with control food from the diet and there was also slight contamination of the urine. Prior to analysis, food was therefore separated from the urine by 5 minutes centrifugation at 1500 rpm. The food pellet was discarded. Contaminating particulate food was removed from the faeces using forceps and the stool sample weighed.

Total faecal samples from each animal were mixed to ensure a homogeneity and duplicate one gram aliquots weighed. The percentage hydration of the stool was calculated following freeze drying to constant weight.

For measurement of total faecal phosphate and metal ion content, freeze dried faeces was ground with a mortar and pestle and 200 mg hydrolysed by heating to 70° C. for 4 hours with 7 ml concentrated nitric acid in polypropylene test tubes. The faecal digests were diluted to 50 ml with de-ionised water in acid washed 125 ml Nalgene containers.

For measurement of soluble faecal phosphate and metal ion content, a 1.5 gram aliquot of stool was suspended in 15 ml deionised water. Following homogenisation and centrifugation at 3000 rpm for 45 minutes, the supernatant was filtered through glass wool to remove contaminating particulate matter and stored at −20° C.

Analytical Methods

Phosphate, iron and calcium were determined in the faecal digest solutions, urine and serum using standard Boehringher Mannheim chemistry on a Hitachi 911 autoanalyser. Magnesium was measured in the faecal digest solutions, urine and serum using flame photometry atomic absorption spectrometry. Urine and serum aluminium were measured using graphite furnace atomic absorption spectrometry.

Differences between treatment groups was assessed using Students t-test with p<0.05 being considered significant.

Procedure

All animals were weighed daily during the course of the study to ensure that food modified by the addition of phosphate binding compounds did not affect weight gain. During the seven day equilibration period, groups of animals treated with CTFeCa, CTFeMg, Mg(OH)$_2$, CaCO$_3$ or CT100 showed a range of mean weight gains from 38–53 grams. Rats treated with Al(OH)$_3$ showed a mean weight gain of 3 grams. The control group demonstrated a reluctance to eat the standard RMI diet (without addition of phosphate binders). After four days, it was necessary to switch them to a control diet (Lilico). These control animals showed a mean weight loss of 17.5 grams during this seven day period. Soluble phosphate was measured in the Lilico diet and found to be 6.8 $\mu$mol g$^{-1}$, similar to that of the RMI diet without addition of binders, 7.5 $\mu$mol g$^{-1}$.

Following feeding with the modified diets for 7 days, animals were transferred to metabowls for collection of total 24 hour faecal and urine excretion. To ensure that any contamination of faeces and urine by food was similar for the different groups, each animal was given a restricted 18 grams of control diet (Lilico). During this period, control animals gained a mean of 3 grams in weight. Other animal groups showed a mean weight loss of 2–22 grams.

Results

Measurement of Urine and Faecal Phosphate Excretion.

Reduced phosphate absorption achieved when a dosage of the inorganic compound is ingested with food is manifested by a low urine phosphate content, a high total faecal phosphate content and a low ratio of soluble faecal phosphate content: total faecal phosphate content (Table 11).

Differences in urinary phosphate concentration between animals groups could be explained by significant differences in urine volume. Renal phosphate excretion was therefore expressed as total ($\mu$mol) per 24 hours. Animals treated with Al(OH)$_3$ and CaCO$_3$ excreted 1259±279 $\mu$mol phosphate and 857±25 $\mu$mol phosphate (mean±SEM) respectively (FIG. 9, Table 11). These values were significantly higher than from rats treated with CTFeCa, CTMgFe, CT100 or Mg(OH)$_2$ mean 71±44 $\mu$mol, 13±4 $\mu$mol, 26±11 $\mu$mol and 65±53 $\mu$mol phosphate respectively. No group treated with phosphate binding compounds showed a significant difference in urinary phosphate excretion compared to the controls, mean 466±188 $\mu$mol. This may be explained by a lower food intake by the control animals, demonstrated by their mean weight loss over the course of the study.

To indicate whether phosphate binders were precipitating phosphate in the rat gastrointestinal tract, total stool phosphate (bound and soluble) and soluble stool phosphate (unbound) were measured. To control for variations in faecal output and faecal hydration between groups, faecal phosphate was expressed as $\mu$mol phosphate g$^{-1}$ dry weight faeces. Total (soluble and insoluble) phosphate g$^{-1}$ dry weight faeces did not differ significantly between any of the treatment groups. Faeces from animals treated with CTFeCa contained significantly less soluble phosphate than the controls or the animals treated with CaCO$_3$ (Table 11). Mean soluble phosphate g$^{-1}$ dry weight faeces as a percentage of mean total phosphate g$^{-1}$ dry weight faeces was 41.9%, 44.8%, 55.9%, 60.7% and 45.0% for animals treated with CTFeCa, Mg(OH)$_2$, Al(OH)$_3$, CT100 and CTFeMg respectively. Soluble phosphate consisted of 79.0% of the total in the control group and 85.5% of the total in the CaCO$_3$ treated group (FIG. 10). These results demonstrate the effectiveness of the CT compounds as binders, decreasing the available phosphate compared to controls and CaCO$_3$ treated animals.

TABLE 11

Mean (±1 SEM) urine and faecal phosphate excretion for control rats and those treated with phosphate binding compounds.

|  | Control | Al(OH)$_3$ | CaCO$_3$ | CTFeCa | Mg(OH)$_2$ | CT100 | CTFeMg |
|---|---|---|---|---|---|---|---|
| Urine phosphate $\mu$mol (n = 4) | 466 ± 188* | 1259 ± 279 | 857 ± 25 | 72 ± 44* | 65 ± 53* | 26 ± 11* | 13 ± 4* |
| Total faecal phosphate $\mu$mol g$^{-1}$ dry weight faeces (n = 4) | 150 ± 32 | 188 ± 26 | 213 ± 16 | 181 ± 12 | 183 ± 17 | 181 ± 40 | 206 ± 34 |
| Soluble faecal phosphate $\mu$mol g$^{-1}$ dry weight faeces (n = 4) | 120 ± 6 | 96 ± 9 | 181 ± 9Δ | 73 ± 12φ | 87 ± 14 | 100 ± 15 | 128 ± 8 |

*p < 0.05 compared to Al(OH)$_3$ and CaCO$_3$ treated animals.
Δp < 0.05 compared to all groups
φp < 0.05 compared to Control and CTFeMg treated animals.

Measurement of Metal Extraction and Retention

Urine Aluminium Excretion, Serum Aluminium Concentration

Urine and serum aluminum concentrations were measured using graphite furnace atomic absorption spectroscopy. For the animals taking Al(OH)$_3$ or CT100, mean serum aluminum concentrations were not significantly higher than serum aluminum from control animals (Table 12). Surprisingly, animals treated with CTFeCa and CTFeMg showed the highest mean serum aluminum concentrations, both significantly higher than animals treated with Mg(OH)$_2$, Al(OH)$_3$, CaCO$_3$ or controls.

Due to significant differences in total urine volume between different animal groups, aluminium was expressed as $\mu$g excreted. For animals treated with Al(OH)$_3$, mean urinary Al$^{3+}$ excretion was at least 2 fold higher than animals treated with any other phosphate binder (Table 12). The animals treated without binders (control diet) surprisingly excreted more aluminium than the animals treated with Al(OH)$_3$.

Measurement of Urine Calcium Excretion, Serum Calcium Concentration

Total urinary calcium excretion from CaCO$_3$ treated animals was not significantly different to controls or animals treated with CTFeCa or Al(OH)$_3$. CaCO$_3$ treated animals excreted significantly more calcium than animals treated with MgOH$_2$, CT100 or CTFeMg (Table 13).

Control animals and those treated with Al(OH)$_3$ had significantly higher serum calcium concentrations than animals supplied with any other treatment (Table 13). Rats treated with CaCO$_3$ had significantly higher serum calcium than those treated with Mg(OH)$_2$, CT100 or CTFeCa.

Measurement of Urine Magnesium Excretion

Urinary magnesium excretion following treatment with the compounds CT100 and CTFeMg was higher although not significantly so compared to the control animals (Table 14). Following Mg(OH)$_2$ administration, urine magnesium excretion was significantly higher than the control group or animals treated with any other binder.

Measurement of Urinary and Serum Iron Concentration

In all urine samples from all treatment groups, iron concentration was at the limit of detection of the method employed (>1 μmol l$^{-1}$).

Release of iron from the phosphate binders was of concern and so serum iron concentrations were measured in all animals. There was however no significant difference in serum iron concentration between any of the treatment groups (Table 14).

TABLE 12

Mean (±1 SEM) urine aluminium excretion, mean (±1 SEM) serum aluminium concentration for control rats and those treated with phosphate binding compounds.

| Treatment | Urine aluminium μg (all n = 4) | Serum aluminium μmol l$^{-1}$ |
| --- | --- | --- |
| Control | 1.23 ± 0.05α | 0.45 ± 0.04 |
| Al(OH)$_3$ | 1.07 ± 0.38β | 0.38 ± 0.03 |
| CaCO$_3$ | 0.50 ± 0.21 | 0.33 ± 0.05 |
| CTFeCa | 0.18 ± 0.12 | 0.66 ± 0.07* |
| Mg(OH)$_2$ | 0.17 ± 0.07 | 0.35 ± 0.08 |
| CT100 | 0.26 ± 0.09 | 0.65 ± 0.24 |
| CTFeMg | 0.31 ± 0.09 | 0.65 ± 0.05* |

*$p < 0.05$ compared to Mg(OH)$_2$, Al(OH)$_3$, CaCO$_3$ and control treated animals
α $p < 0.05$ compared to Mg(OH)$_2$, Al(OH)$_3$, CaCO$_3$, CTFeMg, CT100 and CTFeCa treated animals
β $p < 0.05$ compared to Mg(OH)$_2$, Al(OH)$_3$, CTFeMg, CT100 and CTFeCa treated animals

TABLE 13

Mean (±1 SEM) urine calcium excretion, mean (±1 SEM) serum calcium concentration for control rats and those treated with phosphate binding compounds.

| Treatment | Urine calcium μmol | Serum calcium mmol l$^{-1}$ |
| --- | --- | --- |
| Control | 317 ± 94 | 3.29 ± 0.16 (n = 3)α |
| Al(OH)$_3$ | 539 ± 242 | 3.27 ± 0.07 (n = 3)α |
| CaCO$_3$ | 472 ± 17* | 2.93 ± 0.09 (n = 4)β |
| CTFeCa | 333 ± 80 | 2.48 ± 0.10 (n = 4) |
| Mg(OH)$_2$ | 360 ± 62 | 2.58 ± 0.05 (n = 3) |
| CT100 | 314 ± 20 | 2.54 ± 0.07 (n = 4) |
| CTFeMg | 300 ± 34 | 2.69 ± 0.07 (n = 4) |

*$p > 0.05$ compared to CT100, Mg(OH)$_2$ and CTFeMg treated animals
α $p > 0.05$ compared to CTFeCa, Mg(OH)$_2$, CT100 and CTFeMg treated animals
β $p < 0.05$ compared to Mg(OH)$_2$, CT100 or CTFeCa treated animals

TABLE 14

Mean (±1 SEM) urine magnesium excretion, mean (±1 SEM) serum iron concentration for control rats and those treated with phosphate binding compounds.

| Treatment | Urine magnesium μmol (all n = 4) | Serum iron mmol l$^{-1}$ |
| --- | --- | --- |
| Control | 6.3 ± 1.8 | 37.8 ± 11.2 (n = 3) |
| Al(OH)$_3$ | 9.7 ± 0.6 | 38.5 ± 15.9 (n = 3) |
| CaCO$_3$ | 8.7 ± 1.8 | 41.9 ± 10.8 (n = 4) |
| CTFeCa | 5.9 ± 1.2 | 23.9 ± 5.1 (n = 4) |
| Mg(OH)$_2$ | 17.3 ± 2.3* | 29.4 ± 7.9 (n = 3) |
| CT100 | 9.2 ± 0.6 | 39.5 ± 10.8 (n = 4) |
| CTFeMg | 11.4 ± 0.7 | 48.5 ± 12.5 (n = 3) |

*$p < 0.05$ compared to all groups

Discussion of Results

As phosphate binders are administered in relatively large doses over long periods of time, metal ion release, absorption and toxicity is of prime concern. Serum aluminium concentration in Al(OH)$_3$ or CT100 treated animals was not significantly higher than animals treated with any other binder. This is in agreement with a human study which reported no increase in serum aluminum, measured up to seven hours after administration of 6 grams hydrotalcite (CT100) [Van der Voet and de Wolff, Clin. Tox. (1986–87), 24, 545–553]. As only ~0.1% of an ingested aluminum dose is absorbed [Powell and Thompson, Proc. Nutr. Soc., (1993) 52, 241–253], changes in the large serum volume are at the limits of accurate measurement.

We therefore measured urinary aluminium excretion as an indicator of intestinal uptake. Animals treated with Al(OH)$_3$ excreted at least 2 fold more aluminium than those treated with any other binder and four fold more than CT100 treated rats. Conclusions as to the relative benefits of CT100 in terms of aluminium release are however limited due to the high urinary excretion from the controls.

Release and absorption of iron from the CTFeCa and CTFeMg binders was of concern as body iron content is regulated by absorption from the gastrointestinal tract [McCance and Widdowson, Lancet, (1937) 2, 680–684]. There is no physiological route by which it can be excreted and daily losses are low, urine <0.1 mg, skin losses 0.2–0.3 mg and faeces 0.6 mg [Bothwell, Nutr. Ron. (1995), 53, 237–245]. Animals treated with CTFeCa or CTFeMg did not show an increase in serum iron compared to animals treated with non iron containing binders or controls and as expected, urine iron excretion was at the limit of detection in all groups.

Compared to animals treated with any other binder, there was at least a 66% and 113% increase in soluble faecal iron in CTFeCa or CTFeMg treated animals respectively. Whether this was absorbable was beyond the scope of this study as complex factors including diet and iron store size influence non-haem iron uptake [Bothwell, Supra: Cook, Am. J. Clin. Nutr. (1990), 51, 301–308]. However, as a number of haemodialysis patients are anaemic, an increased iron load may be beneficial [Remussi and Rossi, in The Kidney (Ed. Brenner, BM), W. B. Saunders, Philadelphia, (1996), Chapter 50, pp 2170–2186].

Different magnesium salts have been shown to have efficacy as phosphate binders. Magnesium carbonate has been shown to be an efficient binder [O'Donovan et. al., Lancet, (1986), 51, 880–881] while magnesium hydroxide has been shown to be ineffective or poorly tolerated [Guillot et al., Nephron, (1982), 30, 114–117; Oe et al., Colin. Nephrol, (1987), 28, 180–185]. Care must be taken though to avoid over administration due to the laxative effects of magnesium. In this study none of the animal groups treated with Mg(OH)$_2$, CT 100 or CTFeMg showed an increase in faecal hydration compared to the controls suggesting a dose that was well tolerated by the animals. Neither urine nor serum magnesium were elevated in CTFeMg or CT100 treated animals, suggesting that Mg absorption from these compounds was low. In summary, CT100, CTFeMg and CTFeCa are all high capacity phosphate binders when administered in vivo to rats at low doses. This study indicates they are likely to have limited toxicity although long time course studies are required to evaluate iron, aluminium and magnesium absorption. These compounds may present effective alternatives to the currently prescribed phosphate binders.

What is claimed is:

1. A method for treating hyperphosphataemia, in an animal in need thereof, which comprises administering to said animal, a therapeutically effective amount of a solid mixed metal compound having a phosphate binding capacity, and comprising the compound obtained as a precipitate from a solution of a mixture of metallic salts, free from aluminum, and containing iron (III) and at least one additional metal selected from the group consisting of magnesium, calcium, lanthanum and cerium, said compound having a phosphate binding capacity of at least 30%, as measured by any of the following tests methods (1) or (2), over a pH range of from 3 to 7;

(1) adding 1 gram of said solid mixed metal compound to 25 ml of 40 mmol $l^{-1}$ sodium phosphate buffer solution, homogenizing and gently agitating at room temperature of 30 minutes, centrifuging at 3000 rpm for 5 minutes, filtering through 0.22 µm millipore filter and measuring the soluble phosphate in the supernatant thus produced;

(2) adding 1 gram of said solid mixed metal compound to 25 ml of 20 mmol $l^{-1}$ sodium phosphate buffer solution, homogenizing and gently agitating at room temperature for 30 minutes, centrifuging at 3000 rpm for 5 minutes, filtering through 0.22 µm millipore filter and measuring the soluble phosphate 1 the supernatant thus produced.

2. Method according to claim 1 wherein the solid mixed metal compound containing hydroxyl ions and/or carbonate ions.

3. Method according to claim 2, wherein the solid mixed metal compound further contains sulphate, chloride, oxide or mixtures thereof.

4. The method of claim 1 wherein said animal is a human.

5. A method for treating hyperphosphataemia, in an animal in need thereof, which comprises administering to said animal, a therapeutically effective amount of a solid mixed metal oxide compound having phosphate binding capacity, and comprising the compound obtained as a precipitate from a solution of a mixture of metallic salts, free from aluminum, and containing iron (III) and at least one additional metal selected from the group consisting of magnesium, calcium, lanthanum and cerium, said compound having a phosphate binding capacity of at least 30%, as measured by any of the following test methods (1) or (2), over a pH range of from 2 to 8;

(1) adding 1 gram of said solid mixed metal compound to 25 ml of 40 mmol $l^{-1}$ sodium phosphate buffer solution, homogenizing and gently agitating at room temperature of 30 minutes centrifuging at 3000 rpm for 5 minutes, filtering through 0.22 µm millipore filter and measuring the soluble phosphate in the supernatant thus produced;

(2) adding 1 gram of said solid mixed metal compound to 25 ml of 20 mmol $l^{-1}$ sodium phosphate buffer solution, homogenizing and gently agitating at room temperature for 30 minutes, centrifuging at 3000 rpm for 5 minutes, filtering through 0.22 µm millipore filter and measuring the soluble phosphate in the supernatant thus produced.

6. Method according to claim 5, wherein the solid mixed metal compound contains hydroxyl ions and/or carbonate ions.

7. Method according to claim 6, wherein the solid mixed metal compound further contains sulphate, chloride, oxide or mixture thereof.

8. The method of claim 5 wherein said animal is a human.

9. A method for treating hyperphosphataemia, in an animal in need thereof, which comprises administering to said animal, a therapeutically effective amount of a solid mixed metal compound having phosphate binding capacity, and comprising a hydroxy carbonate containing iron (III) and magnesium metals, further containing sulphate, chloride, oxide or mixtures thereof and free from aluminum, and having a phosphate binding capacity of at least 30% by weight, as measured by any of the test methods (1) or (2), over a pH range of 2 to 8;

(1) adding 1 gram of said solid mixed metal compound to 25 ml of 40 mmol $l^{-1}$ sodium phosphate buffer solution, homogenizing and gently agitating at room temperature of 30 minutes, centrifuging at 3000 rpm for 5 minutes, filtering through 0.22 µm millipore filter and measuring the soluble phosphate in the supernatant thus produced;

(2) adding 1 gram of said solid mixed metal compound to 25 ml of 20 mmol $l^{-1}$ sodium phosphate buffer solution, homogenizing and gently agitating at room temperature for 30 minutes, centrifuging at 3000 rpm for 5 minutes, filtering through 0.22 µm millipore filter and measuring the soluble phosphate in the supernatant thus produced.

10. The method of claim 9 wherein said animal is a human.

* * * * *

UNITED STATES PATENT AND TRADEMARK OFFICE
CERTIFICATE OF CORRECTION

PATENT NO. : 6,926,912 B1
DATED : August 9, 2005
INVENTOR(S) : Norman R. Roberts et al.

It is certified that error appears in the above-identified patent and that said Letters Patent is hereby corrected as shown below:

Column 21,
Line 50, delete "oxide.".

Signed and Sealed this

Twenty-first Day of February, 2006

JON W. DUDAS
*Director of the United States Patent and Trademark Office*